(12) United States Patent
Oates

(10) Patent No.: US 8,939,955 B2
(45) Date of Patent: Jan. 27, 2015

(54) ABSORBENT ARTICLE WITH CONTRASTING WRAPPER GRAPHICS

(75) Inventor: Susan Mary Oates, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 575 days.

(21) Appl. No.: 13/152,493

(22) Filed: Jun. 3, 2011

(65) Prior Publication Data

US 2012/0310201 A1    Dec. 6, 2012

(51) Int. Cl.
*A61F 13/84*    (2006.01)
*A61F 13/551*    (2006.01)

(52) U.S. Cl.
CPC ............ *A61F 13/84* (2013.01); *A61F 13/5514* (2013.01); *A61F 2013/8497* (2013.01)
USPC ................................ 604/385.02; 604/385.19

(58) Field of Classification Search
USPC .......................... 604/385.02, 385.19, 385.201
See application file for complete search history.

(56) References Cited

U.S. PATENT DOCUMENTS

| | | |
|---|---|---|
| 5,839,585 A | 11/1998 | Miller |
| D409,389 S | 5/1999 | May et al. |
| D433,796 S | 11/2000 | Zack |
| D439,735 S | 4/2001 | Velazquez et al. |
| D440,398 S | 4/2001 | Mitchler et al. |
| 6,454,095 B1 | 9/2002 | Brisebois et al. |
| 6,520,330 B1 | 2/2003 | Batra |
| 6,708,823 B2 | 3/2004 | Cottingham et al. |
| 6,923,321 B2 | 8/2005 | Samolinski et al. |
| 7,172,073 B2 | 2/2007 | Hanson |
| 7,356,182 B1 | 4/2008 | Fleisher et al. |
| D656,013 S | 3/2012 | Norman et al. |
| D656,396 S | 3/2012 | Palmieri et al. |
| D658,056 S | 4/2012 | Hughes et al. |
| 8,157,777 B2 * | 4/2012 | Ito et al. ................... 604/385.02 |
| D659,011 S | 5/2012 | Lee |
| 2002/0027563 A1 | 3/2002 | Van Doan et al. |
| 2002/0072723 A1 | 6/2002 | Ronn et al. |
| 2002/0148749 A1 | 10/2002 | Briseboi et al. |
| 2003/0088224 A1 | 5/2003 | Ceman et al. |
| 2003/0097109 A1 | 5/2003 | Bruce et al. |

(Continued)

FOREIGN PATENT DOCUMENTS

| | | |
|---|---|---|
| EP | 1 295 711 A1 | 3/2003 |
| EP | 1 873 071 A1 | 1/2008 |

(Continued)

OTHER PUBLICATIONS

Pieters, Rik et al., "The Stopping Power of Advertising: Measures and Effects of Visual Complexity," Journal of Marketing, vol. 74, No. 5, Sep. 1, 2010, pp. 48-60.

(Continued)

*Primary Examiner* — Susan Su
(74) *Attorney, Agent, or Firm* — Kimberly-Clark Worldwide, Inc.

(57) ABSTRACT

A product includes an absorbent article contained within a pouch. The absorbent article includes a first graphic and the pouch includes a second graphic which is different than the first graphic. The pouch is at least partially translucent and the absorbent article is arranged in the pouch such that at least a portion of the first graphic is visible through the pouch. The first graphic defines a first complexity value and the second graphic defines a second complexity value wherein the difference between the first complexity value and the second complexity value is at least 1.2.

19 Claims, 16 Drawing Sheets

(56) References Cited

U.S. PATENT DOCUMENTS

| | | |
|---|---|---|
| 2003/0127351 A1 | 7/2003 | Takahashi et al. |
| 2004/0102748 A1 | 5/2004 | Hirotsu |
| 2004/0238393 A1* | 12/2004 | Ohi et al. ................. 206/438 |
| 2005/0145523 A1 | 7/2005 | Zander et al. |
| 2005/0148979 A1* | 7/2005 | Palma et al. ............ 604/385.02 |
| 2005/0154365 A1 | 7/2005 | Zander et al. |
| 2006/0025739 A1* | 2/2006 | DiPalma et al. ......... 604/385.02 |
| 2006/0091036 A1 | 5/2006 | Casella |
| 2007/0032768 A1* | 2/2007 | Cohen et al. ............ 604/385.01 |
| 2007/0142810 A1* | 6/2007 | Visscher ................. 604/385.06 |
| 2007/0235263 A1 | 10/2007 | Legault et al. |
| 2007/0251851 A1 | 11/2007 | Warren et al. |
| 2007/0267322 A1 | 11/2007 | Kishida et al. |
| 2008/0097364 A1 | 4/2008 | Yang |
| 2009/0084698 A1* | 4/2009 | Ito et al. .................. 206/438 |
| 2009/0120834 A1 | 5/2009 | Ruman et al. |
| 2009/0127322 A1 | 5/2009 | Miller |
| 2009/0266733 A1 | 10/2009 | Betts et al. |
| 2010/0147721 A1 | 6/2010 | Molina et al. |
| 2010/0195916 A1 | 8/2010 | Blondiaux et al. |
| 2011/0120897 A1 | 5/2011 | Takahashi |
| 2011/0253578 A1 | 10/2011 | Benson et al. |
| 2011/0270208 A1* | 11/2011 | Miura et al. ............ 604/385.02 |
| 2012/0016327 A1 | 1/2012 | Mason et al. |
| 2013/0190711 A1* | 7/2013 | Hashino et al. ......... 604/385.02 |

FOREIGN PATENT DOCUMENTS

| | | |
|---|---|---|
| EP | 1 994 917 A1 | 11/2008 |
| EP | 1 994 918 A1 | 11/2008 |
| EP | 1 828 011 B1 | 10/2009 |
| EP | 1 833 444 B1 | 12/2010 |
| WO | WO 02/30347 A1 | 4/2002 |
| WO | WO 2009/077897 A2 | 6/2009 |

OTHER PUBLICATIONS

Co-pending U.S. Appl. No. 29/393,396, filed Jun. 3, 2011, by Oates et al. for "Feminine Care Package."

Co-pending U.S. Appl. No. 13/153,032, filed Jun. 3, 2011, by Oates et al. for "Package with Contrasting Graphics."

* cited by examiner

ABSORBENT ARTICLE WITH CONTRASTING WRAPPER GRAPHICS

BACKGROUND OF THE INVENTION

Typically, absorbent articles such as pads or pantiliners include one or more elements, such as an outer cover, an absorbent core, a body side liner and a peel strip. Such articles are often individually wrapped in a pouch or similar wrapper, or are wrapped as a group of articles. A plurality of articles, whether or not individually wrapped, is also typically sold in bulk packaging, such as a bag or box.

The past wrappers/pouches were opaque and were designed to hide the silhouette of the absorbent article contained within the wrapper/pouch and the absorbent articles were all white. A recent trend has been to use less opaque and more translucent wrapper/pouch materials that are less expensive. However, these wrapper/pouch materials do not adequately hide the silhouette of the absorbent article. This inability to hide the silhouette has worsened as color and graphics have been added to absorbent articles to improve their aesthetic appearance. These colors and graphics tend to further highlight the absorbent article silhouette within the wrapper/pouch.

To address this issue of inadequate hiding of the absorbent article silhouette, some have added color and graphics to the wrapper/pouch material. Often the absorbent article and wrapper/pouch material are designed with similar or matching graphics and color. As such, the wrapped absorbent article now has a uniform external appearance that hides the silhouette of the absorbent article but highlights the silhouette of the wrapper/pouch.

In general, consumers do not want others to know that they are carrying an absorbent article. Thus, graphic patterns that highlight the silhouette of the wrapped absorbent article are less desirable because others can identify the absorbent article and/or pouch from its silhouette. Therefore there is a need for graphic patterns printed on the absorbent articles and the wrapper/pouch that together hide the silhouette of the absorbent article and the wrapper/pouch.

SUMMARY OF THE INVENTION

In one aspect, the present invention provides a product including a single absorbent article contained within a pouch. The absorbent article includes a first graphic and the pouch includes a second graphic which is different than the first graphic. The pouch is at least partially translucent and the absorbent article is arranged in the pouch such that at least a portion of the first graphic is visible through the pouch. The first graphic defines a first complexity value and the second graphic defines a second complexity value. The difference between the first complexity value and the second complexity value is at least 1.2.

In various embodiments, the second graphic is aligned to at least partially overlay the first graphic to create a compound coordinated graphic.

In some embodiments, the first graphic defines a first complexity value of at least 3 or at least 5. In some embodiments, the second graphic defines a second complexity value of no more than 1.3.

In other embodiments, the first graphic defines a first complexity value of no more than 1.3. In these embodiments, the second graphic defines a second complexity value of at least 3.

In some embodiments, the first graphic is printed on a peel strip and the entire peel strip defines a first complexity value of at least 3. Likewise, the second graphic is printed on the pouch and the entire pouch defines a second complexity value of no more than 1.6.

In some embodiments, the first graphic is printed on a peel strip and the entire peel strip defines a first complexity value of no more than 1.6. Likewise, the second graphic is printed on the pouch and the entire pouch defines a second complexity value of at least 3.

In some embodiments, the absorbent article includes a baffle and a peel strip. The baffle and the peel strip combine to create an initial garment-facing surface. The first graphic is printed on the peel strip and the baffle and the entire initial garment-facing surface defines a first complexity value of at least 3. The second graphic is printed on the wrapper and the entire wrapper defines a second complexity value of no more than 1.6.

In various embodiments, the difference between the first complexity value and the second complexity value is at least 3. In some embodiments, the first graphic defines a first number of printed colors and the second graphic defines a second number of printed colors. The difference between the first number of printed colors and the second number of printed colors is at least 2.

In another aspect, the present invention provides a product that includes a single absorbent article contained within a pouch. The absorbent article includes a first graphic and the pouch includes a second graphic which is different than the first graphic. The pouch is at least partially translucent such that the first graphic is visible through the pouch. The first graphic defines a first number of printed colors and the second graphic defines a second number of printed colors. The difference between the first number of printed colors and the second number of printed colors is at least one. In some embodiments, the first number of printed colors is one and the second number of printed colors is at least three.

In some embodiments, the first graphic has a lowest L* value and the second graphic has a lowest L* value that is at least 10 different than the lowest L* value of the first graphic.

In some embodiments, the first graphic is comprised of a first total number of inks and the second graphic is comprised of a second total number of inks. The difference between the first total number of inks and the second total number of inks is at least two.

In another aspect, the present invention provides a product that includes a single absorbent article contained within a pouch. The absorbent article includes a first graphic and the pouch includes a second graphic which is different than the first graphic. The pouch is at least partially translucent such that the first graphic is visible through the pouch. The first graphic includes a first total number of colors having a lowest L* value. The second graphic includes a second total number of colors having a lowest L* value. The difference between the lowest L* value of the first graphic and the lowest L* value of the second graphic is at least 10.

In various embodiments, the first graphic includes a first total number of inks and the second graphic includes a second total number of inks. The difference between the first total number of inks and the second total number of inks is at least two.

In some embodiments, the first number of printed colors is one and the second number of printed colors is at least three.

In some embodiments, the first graphic defines a first complexity value and the second graphic defines a second complexity value. The difference between the first complexity value and the second complexity value is at least 2.

DEFINITIONS

Figure 1:
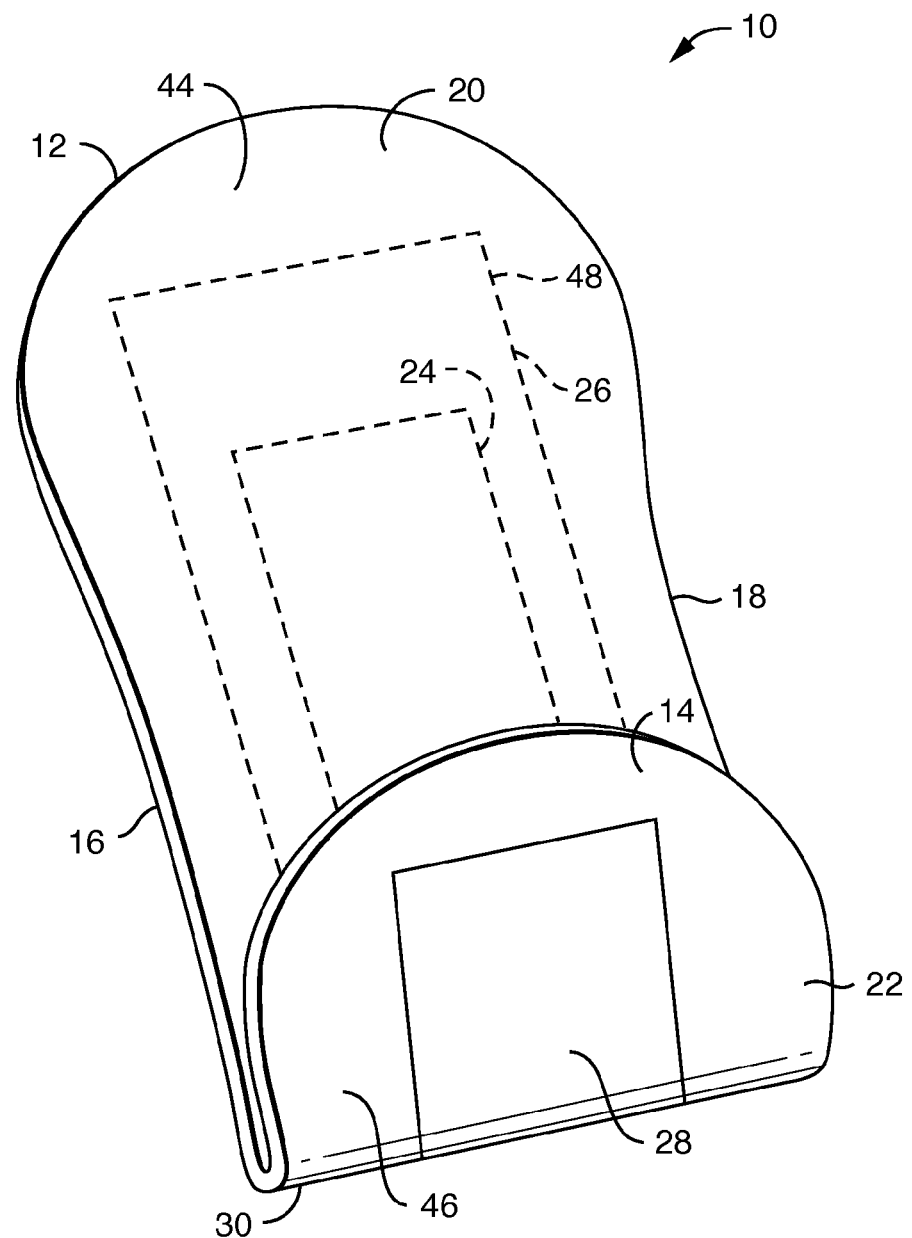
FIG. 1 is a perspective view of an exemplary article in a partially folded configuration.

As used herein, the term "article" or "article component" is used to describe an item which is to be used by a consumer. For example, absorbent articles include, without limitation, diapers, pull-up type training pant garments, adult incontinence garments, male incontinence products, tampons, vaginal suppositories, pantiliners, female incontinence pads, and sanitary napkins, which are sometimes referred to as "personal care articles" or "absorbent personal care articles". For the purposes of this patent, a separate or individual peel strip which protects the adhesive is considered to be a part of the article. If the peel strip also serves as a wrapper, then the peel strip/wrapper is considered as a packaging component. As used herein, the term "packaging" or "packaging component" is used to describe any items which are associated with the article, but not used within the absorbency purpose of the article. Packaging can be any items which are used to transport, store, protect or hide the article. Examples of packaging include, without limitation, wrappers, pouches, bags, boxes and the like. Typically, boxes or bags are placed on store shelves. Generally, these boxes or bags contain a plurality of absorbent personal care articles. These items may be referred to as an "outer packaging component". In addition, packaging may include an inner wrapper or pouch in which one or more absorbent personal care articles are placed. Wrappers and pouches may be referred to as an "inner packaging component". The wrappers or pouches can be placed into a second packaging component, such as the outer packaging described above. The terms "wrapper" and "pouch" are used interchangeably herein.

As used herein, the term "product" is used to describe the items sold or otherwise, provided to a consumer or user. A product includes an article component and a packaging component.

As used herein, the term "element" is used to describe a separate or individual component of a product or packaging. Product elements may include, for example, a liner, an absorbent core, an outer cover, an attachment system, etc. Packaging elements may include wrapper materials, pouch materials, bag materials, bag handles, wrappers, pouches, bags and the like.

As used herein, the term "visible" is intended to mean attribute of feature which is visually perceived by an individual user or consumer. Generally for a consumer or user, the attribute should be visible in the range of about 0.25 feet (0.075 meters) to about 3 feet (0.91 meters). For a non-consumer or non-user, generally for an attribute to be visible, the distance should be greater than about 3 feet (0.91 meters).

As used herein, "perceived" or "perception" is the ability to recognize an attribute or feature when the visual angle that the attribute or feature subtends is greater than about 5 minutes of visual arc and less than about 45 minutes of visual arc as determined by the following equation:

Minutes of visual arc=3438*(length of the object/ distance from object)

Where

Length of the object=size of the object measured perpendicular to the line of sight Distance from object=distance from the front of the eye to the object along the line of sight A minute of visual arc is $\{\text{fraction } (1/60)\}^{th}$ of 1 degree.

As used herein, the term "color" is intended to mean an individual's perception of the spectral composition of visible light coming from a portion of an object. Color characteristics include hue, saturation and luminosity. Each is a separate color characteristic. Hue is the attribute of a color which allows it to be classified as a given color. Saturation, which is sometimes referred to as vividness, is the intensity of the color. Saturation is the degree of freedom from gray. Luminosity, sometimes referred to as value, is the degree of lightness (paleness) or darkness in a color. For example, a blue with white added is a pale color, e.g., baby blue, and blue with black added is a dark color, e.g., navy blue.

As used herein, the term "form" is used to describe an individual's perception of the spatial variation of visible light due to the bulk shape and structure of a portion of an object in three dimensions. Stated another way, form is shape and structure of an item which distinguishes it from its surrounding which causes a spatially discontinuous change in light that is transmitted through or reflected from an item.

As used herein, the term "pattern" is used to describe the individual's perception of spatial variation of visible light due to contrasts in spatial variation of light due to the color, form, and texture of a portion of an object incorporated into the object by the manufactory of the elements. This contrast creates various visual distinct regions or lines sometimes referred to as "figures" within its surroundings sometimes referred to as "ground." Patterns can be formed by combinations of contrasting color, form, and texture relative to its surroundings. An element can have more than one pattern, but each pattern would be distinguishable, recognizable, and separate from the other patterns on the element. Pattern is also a term used to describe the observer's perception of combined effect of more than one color, form, or texture within a portion of an observer's field of view.

The term "body side" means the side that would face toward the body of the user, regardless of whether an undergarment is actually being worn by the user and regardless of whether there are or may be intervening layers between the component and the body of the user. Likewise, the term "garment side" means the side that faces away from the body of the user, and therefore toward any outer garments that may be worn by the user, regardless of whether the undergarment is actually being worn by a user, regardless of whether any such outer garments are actually worn and regardless of whether there may be intervening layers between the component and any outer garment.

The term "graphic" means a pattern created by printing. In the present invention, when patterns or graphics are printed on a substrate, the color may be printed on the outer surface, on an inner surface or between surfaces of the substrate. For example, in the case of the garment-side outer cover, the color or pattern may be applied to the side of the garment-side outer cover which is positioned during use adjacent the garment or may be applied to the side of the garment side outer cover which is proximate the absorbent core. Alternatively, if the garment side outer cover is a multilayer structure, the color or pattern may be printed between the layers. When printing pouches, the color or pattern may be applied to the outside surface of the pouch, on the inside surface of the pouch or between layers of the pouch if the pouch has multiple layers.

DETAILED DESCRIPTION OF THE DRAWINGS

The present invention provides a compound graphic composed of a first substrate having a first graphic overlaid upon a second substrate having a second graphic wherein the second graphic can be seen through the first substrate and wherein the first graphic and the second graphic combine to provide a compound coordinated graphic. The compound coordinated graphic can be incorporated into disposable products to provide discretion while still providing a high quality look.

Disposable absorbent articles such as, for example, feminine care and incontinent absorbent articles, generally include a liquid pervious topsheet, a substantially liquid impervious backsheet, and an absorbent core positioned and held between the topsheet and the backsheet. The topsheet is generally operatively permeable to the liquids that are intended to be held or stored by the absorbent article, and the backsheet may be substantially impermeable or otherwise operatively impermeable to the liquids intended to be held or stored. Disposable absorbent articles may also include other optional components or layers, such as liquid wicking layers, liquid distribution layers, barrier layers, and the like, as well as combinations thereof, which may improve the fluid handling and storage properties of the disposable absorbent article. Generally, disposable absorbent articles and the components thereof provide a body-facing surface and a garment-facing surface. As an alternative, the substantially liquid impervious backsheet may be replaced with a liquid pervious backsheet. When a liquid pervious backsheet is used, generally the absorbent personal care article may be used in conjunction with another liquid impervious layer or article, such as liquid impervious pants.

Figure 2:
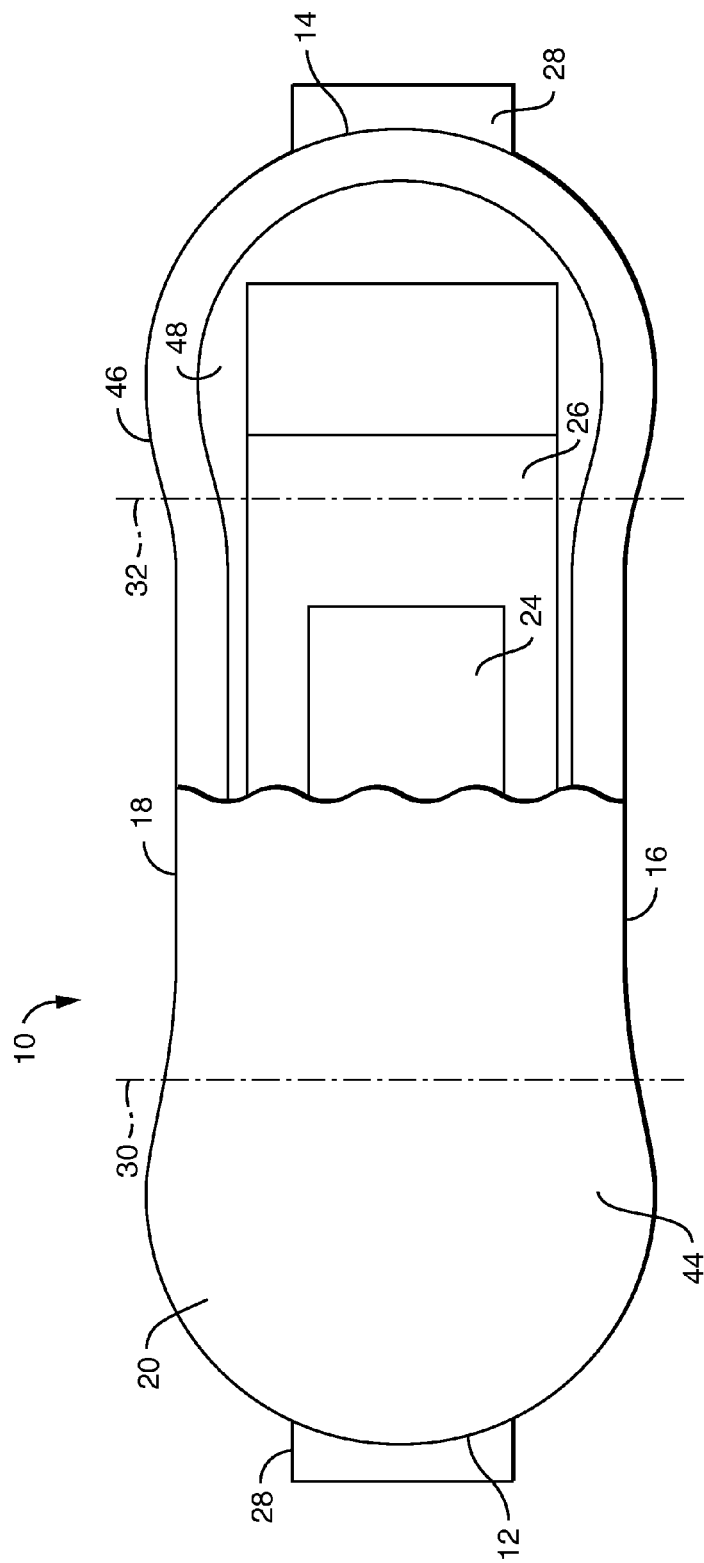
FIG. 2 is a body-side plan view of another exemplary article with portions cut away to better illustrate underlying features.

To obtain a better understanding of the absorbent articles of the present invention, which may be present in a wrapper/pouch component as the packaging component, attention is directed to FIGS. 1 and 2. Specifically, FIG. 1 is a perspective view of an exemplary article in a partially folded configuration and FIG. 2 is a body-side plan view of another exemplary article with portions cut away to better illustrate underlying features. In FIGS. 1 and 2, exemplary absorbent articles 10 are shown as including an outer cover 46 (otherwise referred to as a baffle or backsheet), an absorbent core 48, an optional tissue layer 26, an optional surge layer or optional distribution layer 24 and a body-side liner 44 (also referred to as the top sheet). The absorbent articles 10 also have a first side 16 and a second side 18. The first and second sides 16, 18, respectively, are the longitudinal sides of the elongated absorbent articles. The sides can be contoured, for example in a concave shape, or they can be linear. The sides can further include flaps (not shown) that extend laterally outward. Flaps are known in the art and are shown in, for example, U.S. Pat. No. 6,387,084 issued to VanGompel et al. In some embodiments (not shown), one or more elastic elements may be disposed along the sides to form a gasket with the body of the user. Elastic sides are known in the art and are shown in, for example, U.S. Pat. No. 6,315,765 issued to Datta et al. In some embodiments, the elastic elements may be disposed between the body side-liner and the outer cover.

The absorbent articles 10 have a body facing surface 20, which usually includes the outer surface of the body side liner 44, and a garment facing surface 22, which usually contains an outer portion of the outer cover 46. Applied to at least a portion of the garment-facing surface 22 may be a garment attachment adhesive. In various embodiments, the garment attachment adhesive is configured as a single band of adhesive or as two or more spaced apart strips. Alternatively, the garment attachment adhesive includes a swirl pattern of adhesive which encompasses a major portion of the garment facing surface 22 of the absorbent articles 10.

A release strip 28, also known as a releasable peel strip, may be removably secured to the garment attachment adhesive and serves to prevent premature contamination of the garment attachment adhesive before the absorbent article 10 is secured to the crotch portion of an undergarment. In various embodiments, the garment attachment adhesive is designed to be secured to the inner crotch portion of an undergarment so as to keep the absorbent article in register with the body of the user. The release strip 28 may extend beyond one or both of the ends 12, 14 of the outer cover, as shown in FIG. 2. As an alternative, the release strip may be shorter than the ends of the outer cover 12 and 14, as shown in FIG. 1.

The body side liner or topsheet 44, which is preferably liquid permeable, may be formed from one or more materials, may include a layer constructed of any operative material, and may be a composite material. For example, the body-side liner can include a woven fabric, a nonwoven fabric, a polymer film, a film-nonwoven fabric laminate or the like, as well as combinations thereof. Examples of a nonwoven fabric useable in the body-side liner or topsheet 44 include, for example, an airlaid nonwoven web, spunbond nonwoven web, meltblown nonwoven web, a bonded-carded-web, hydroentangled nonwoven webs, spunlace webs or the like, as well as combinations thereof. Other examples of suitable materials for constructing the body-side liner or topsheet 44 can include rayon, bonded carded webs of polyester, polypropylene, polyethylene, nylon, or other heat-bondable fibers finely perforated film webs, net-like materials, and the like, as well as combinations thereof. These webs can be prepared from polymeric materials such as, for example, polyolefins, such as polypropylene and polyethylene and copolymers thereof, polyesters in general including aliphatic esters such as polylactic acid, nylon or any other heat bondable materials. In a desired arrangement, the body-side liner or body contacting layer 44 can be configured to be operatively liquid-permeable with regard to the liquids that the article is intended to absorb or otherwise handle. In some embodiments, the operative liquid-permeability may be provided or enhanced by a plurality of pores, perforations, apertures or other openings, as well as combinations thereof, which are present or formed in the liner or body contacting layer.

The baffle or backsheet 46 may include a layer constructed of any operative material, and may or may not have a selected level of liquid-permeability or liquid-impermeability, as desired. In a particular configuration, the baffle or backsheet 46 may be configured to provide an operatively liquid-impermeable baffle structure. The baffle or backsheet 46 may, for example, include a polymeric film, a woven fabric, a nonwoven fabric or the like, as well as combinations or composites thereof. For example, the baffle may include a polymer film laminated to a woven or nonwoven fabric. In a particular feature, the polymer film can be composed of polyethylene, polypropylene, polyester or the like, as well as combinations thereof. Additionally, the polymer film may be micro-embossed, have a printed design, have a printed message to the consumer, and/or may be at least partially colored. Bicomponent films or other multi-component films can also be used, as well as woven and/or nonwoven fabrics which have been treated to render them operatively liquid-impermeable. Other suitable baffle materials include closed cell polyolefin foams. For example, a closed cell polyethylene foam may be employed. Suitably, the baffle or backsheet 46 can operatively permit a sufficient passage of air and moisture vapor out of the article, particularly out of an absorbent (e.g., storage or absorbent core 48) while blocking the passage of bodily liquids. An example of a suitable baffle material can include a breathable, microporous film, such as those described in, for example, U.S. Pat. No. 6,045,900 to McCormack et al.

The liquid permeable body side liner 44 and the liquid-impermeable baffle 46 may be peripherally sealed together to enclose the absorbent core 48 to form the absorbent article 10. Alternatively, the body-side liner or topsheet 44 can be wrapped around both the absorbent core 48 and the baffle or backsheet 46 to form a wrapped pad. The body-side liner 44 and the baffle 46, and other components of the absorbent article, can be joined for example with adhesive bonds, ultrasonic bonds, thermal bonds, pinning, stitching or any other attachment techniques known in the art, as well as combinations thereof.

The absorbent core 48 is designed to absorb body exudates, including menstrual fluid, blood, urine, and other body fluids. The absorbent core 48 may contain one or more layers of absorbent material. The layers can contain similar materials or different materials. Suitable materials for the absorbent core 48 include, for example, cellulose, wood pulp fluff, rayon, cotton, and meltblown polymers such as polyester, polypropylene or coform. Coform is a meltblown air-formed combination of meltblown polymers, such as polypropylene, and absorbent staple fibers, such as cellulose. A preferred material is wood pulp fluff for its low cost, relative ease of formation and good absorbent properties.

The absorbent core 48 can also be formed from a composite comprised of a hydrophilic material which may be formed from various natural or synthetic fibers, wood pulp fibers, regenerated cellulose or cotton fibers, or a blend of pulp and other fibers. A desired material is an airlaid material.

In some embodiments, the absorbent core 48 may also include a superabsorbent material, in addition to or in place of the hydrophilic material, which increases the ability of the absorbent core to absorb a large amount of fluid in relation to its own weight. Generally stated, the superabsorbent material can be a water-swellable, generally water-insoluble, hydrogel-forming polymeric absorbent material, which is capable of absorbing at least about 15, suitably at least about 30, and possibly about 60 times or more its weight in physiological saline (e.g. saline with 0.9 wt % NaCl).

Additional layers or substrates, including for example, the liquid acquisition and distribution layer 24, also referred to as a surge or transfer layer, and an optional tissue layer 26 are also incorporated into the absorbent article, for example, between the body-side liner or topsheet 44 and the absorbent core 48. The distribution layer 24 may be shorter than the absorbent core 48 or have the same length as the absorbent core 48. The distribution layer serves to temporarily hold an insulting fluid to allow the absorbent core sufficient time to absorb the fluid, especially when a superabsorbent material is present. In one embodiment, the absorbent core, distribution layer and other components, such as tissue layers, are free floating (unattached) between the outer cover and the liner, which are secured along only the peripheral edges thereof. Alternatively, the absorbent core, transfer layer and other components are attached to one or both of the outer cover and liner and/or to each other.

Figure 3:
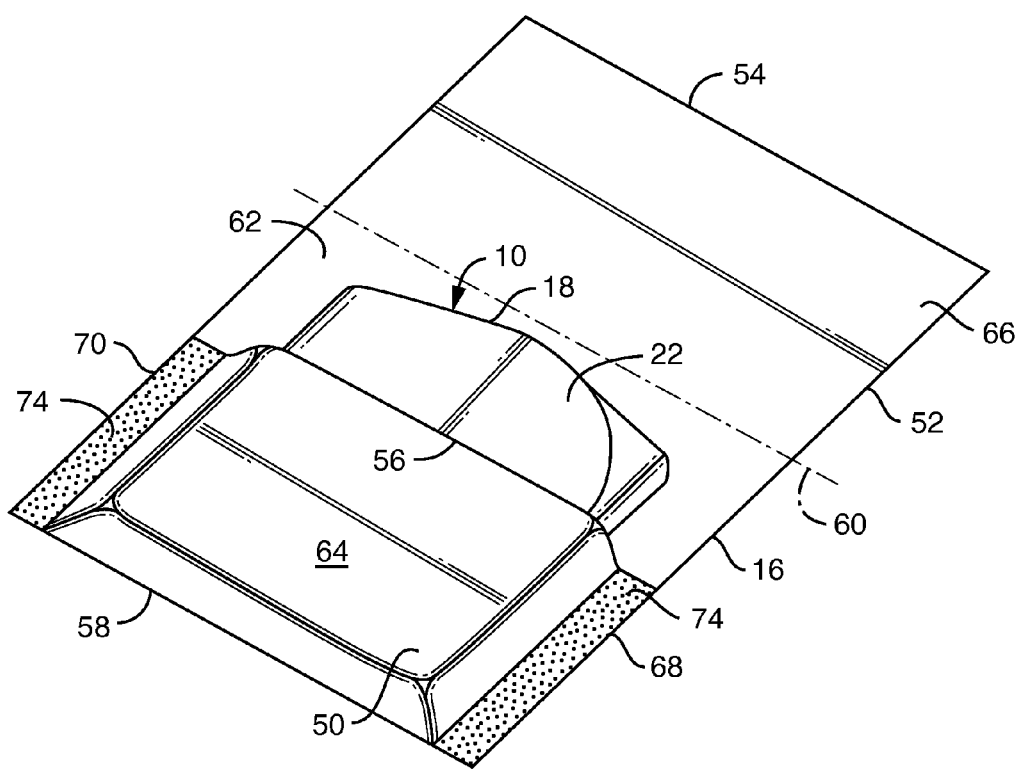
FIG. 3 is a perspective view of an exemplary article partially enclosed in an exemplary wrapper.

Referring to FIG. 1, the absorbent article 10 is shown in a partially folded configuration. Specifically, the absorbent article 10 is shown folded along a fold line 30. Additionally, the absorbent article can be folded along a pair of fold lines 30, 32 (FIG. 2) to form a tri-fold configuration as illustrated in FIG. 3. In other embodiments, the absorbent article can be bi-folded, flattened, rolled, or otherwise suitably configured. The absorbent article is then inserted into a wrapper or pouch, otherwise referred to as an inner wrapper component. A plurality of pouches containing absorbent articles may then be disposed in a package otherwise referred to as an outer packaging component. One article/packaging configuration is shown in U.S. Pat. No. 6,601,706 to McManus, which is hereby incorporated by reference. The articles can be oriented in various ways within the individual packaging component, for example, with the fold lines 30, 32 running parallel or perpendicular to the sides of the individual packaging component 68, 70.

Figure 4:
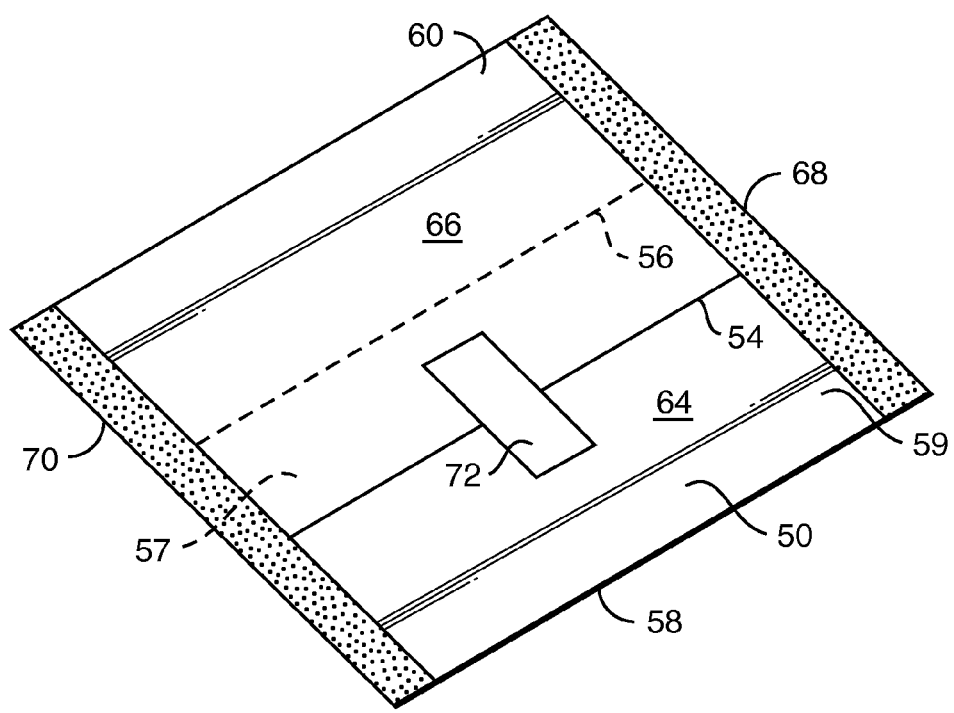
FIG. 4 is a perspective view of an article enclosed in a first exemplary wrapper.
Figure 5:
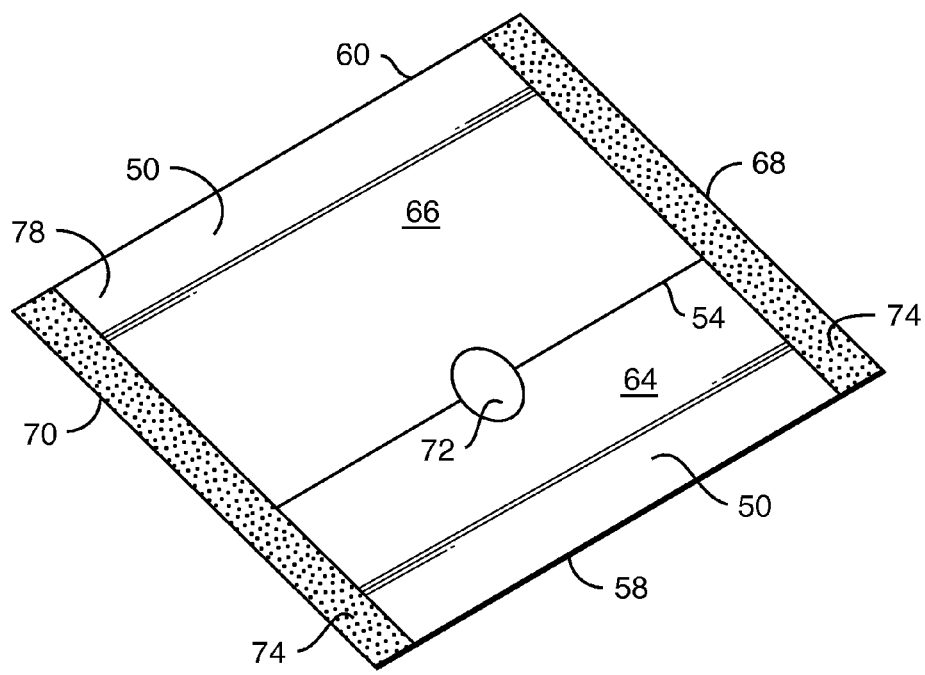
FIG. 5 is a perspective view of an article enclosed in a second exemplary wrapper.

Referring now to FIGS. 3, 4, and 5, the wrapper/pouch component 50 may be formed from a strip or web 52 of material having a first end and a second end having free edges 54, 56 respectively. In various embodiments, the wrapper/pouch component may have different configurations or can be prepared in other ways without departing from the scope of the present invention. The wrapper/pouch component 50 may be formed from a strip or web 52 of material having a first end and a second end having free edges 54, 56 respectively. It should be understood that the term "free edge" refers to an edge that is unattached after the package component is opened, regardless of whether the free edge is attached when the package component is closed. Accordingly, one or both of the free edges may be formed along a perforation line, or may be adhered to an underlying layer, with the edge defined by the perforation line being a "free edge" after the perforation line is broken. The free edge can be a single layer cut or formed edge, or can include a double-layer folded edge, or can include an edge formed by a plurality of layers.

The pouch material can be formed from any suitable material such as non-woven material, films, paper, laminates, and/or cloth (including woven) materials, and combinations thereof. For example, the pouch can be made as disclosed in U.S. Pat. No. 6,716,203, to Sorebo et al., the entire disclosure of which is hereby incorporated herein by reference. In one embodiment, the pouch is made of a film/spunbond laminate material available from Kimberly-Clark Corp., and known as HBSTL ("highly breathable stretch thermal laminate"), and which material is further disclosed in U.S. Pat. No. 6,276,032, to Nortman et al., the entire disclosure of which is hereby incorporated herein by reference. Various embodiments of a non-woven pouch material can have a basis weight less than about 50 gsm, alternatively between about 10 gsm and about 40 gsm. In some embodiments, the pouch material may be a film made of polyethylene, polypropylene, polyester, and the like, and combinations thereof. In some embodiments, the pouch material may be a spunbond-meltblown-spunbond (SMS) laminate having a basis weight of 20 to 40 grams per square meter (gsm). In some embodiments, the basis weight may be 20 to 30 gsm, 22-28 gsm, or 22 to 24 gsm. In a particular embodiment, the wrapper/pouch material is a SMS having a basis weight of 22 gsm. In various embodiments, the wrapper/pouch material may have any suitable translucency such that the graphics discussed herein are visible therethrough. For example, the wrapper/pouch material may have any suitable translucency such that the peel strip graphics and/or the pouch graphics are visible through the wrapper/pouch material prior to opening the pouch/wrapper. One way of quantifying the translucency of a given material is by quantifying the light transmittance through the material. In some embodiments, the wrapper/pouch material may have a light transmittance of at least 30%, at least 40%, at least 50%, at least 60%, at least 70%, at least 80%, or at least 90%. In some embodiments, the wrapper/pouch material may have a light transmittance of about 80 to 90%. The light transmittance may be measured by any suitable method. For example, light transmittance may be measured using a light transmittance analyzer as described in U.S. patent publication 2004/0238393 to Ohi.

Each of the first and second ends is folded along fold lines 58, 60 that define the top and bottom edge of the pouch respectively. The folded pouch has a back panel 62, a first panel 64 and a second panel 66. The first panel 64 and the back panel 62 are secured along the side edges 68, 70 thereof to form a pocket shaped to receive the absorbent article. In one embodiment, the pocket and pouch are shaped and dimensioned to receive a single absorbent article component, which is individually wrapped in the pouch. The second panel 66 is folded over the first panel 64 such that the free edge 54 of the second panel 66 overlies the first panel 64. In this configuration, the second panel 66 acts as a flap. The first panel 64 has a covered or overlapped portion 57 (FIG. 4) extending between the free edge 54 (exterior) and the free edge 56 (interior), which covered or overlapped portion 57 underlies the second panel. In one embodiment, there is no overlap, rather, the free edges 54, 56 abut or are separated by a small distance. In one example, the portion 57 has a length of about 1-50 mm, generally about 2-22 mm and typically about 4-10 mm between the free edges 54, 56. The first panel 64 further includes an uncovered second portion 59 (FIG. 4) extending between the free edge 54 and the fold line 58. Of course, it should be understood that the length and width of the article and packaging components can vary according to the type of article and the size of the article.

As an alternative to having the free edge 54 of the second panel 66 overlap the first panel, the wrapper component can be designed such that there is no overlap between the free edge 54 and the first panel 64, without departing from the scope of the present invention. For example, the free edges 54, 56 may abut each other or are separated by a small distance such that there is a gap between the free edges (not shown). As such, in this alternative, the second panel is defined merely as another panel.

A pair of side seals 74 secures the first panel 64 to the back 62, and the second panel 66 to the back 62 and to the first panel 64. The side seals are desirably formed after the first panel is folded over the back panel and the second panel is folded over the back panel and the first panel. Although, it is possible that the first panel could first be sealed to the back panel, and the second panel then sealed to one or both of the back panel and first panel. In an alternative configuration, the second panel is not sealed at the side edges of the first panel and back panel. The sides may be sealed by any method known to those skilled in the art. Exemplary sealing methods include, for example, adhesive sealing, bonding by the application of heat and pressure, ultrasonic bonding or any other art known bonding methods. In one embodiment of the present invention, the side seals 74 may be frangible, meaning they can be easily broken such that the second panel 66 can be separated from the first panel 64 and back panel 62, and such that the first panel 64 can be easily separated from the back panel 62, wherein the product 10 is exposed for removal from the pouch by the user.

In one embodiment, the second panel 66 is releasably secured to the first panel 64. For example, a fastening element 72, shown as a tab in FIGS. 4 and 5, is secured across the free edge 54 of the second panel 66 to secure the second panel 66 to the first panel 64. The fastening element 72 can be releasably secured to both of the second panel and first panel, or it can be fixedly secured to one of the second panel and first panel and releasably secured to the other. Another possible configuration includes the fastening element fixedly secured to both panels and one or both of the panels are provided with an area of weakness, such as a perforated area, which allows a portion of one or both of the panels to be removed or damaged when the wrapper is opened. The fastening element can be formed as adhesive tape, a snap, a button, a mechanical fastener (e.g., hook and loop), a tie, or as any other device known by those skilled in the art. The fastening element can have various alternative shapes, including but not limited to a square, rectangle, triangle, circle, oval, obround, oblong or diamond shape, or any other irregular shape or pattern. In an alternative embodiment, the fastening element is formed on the inside of the second panel such that it engages the first panel as the second panel is folded thereover and is not visible to the user. The adhesive may be applied as a ribbon, dot, a swirl pattern or any other pattern which effectively adheres the second panel 66 to the first panel 64. In another alternative way to fasten the second panel 66 to the first panel 64, the second panel 66 is simply sealed to the first panel 64 with a heat seal or other weld, with the weld defining the fastening element. In another embodiment, the second panel 66 is not sealed or otherwise attached to the first panel 64, but rather is simply folded thereover. Alternatively, the sides of the second panel are sealed to the back panel and to the first panel, with the side seals being breakable in response to a user grasping and lifting the second panel.

In some embodiments, the second panel 66 is refastenably secured to the first panel 64, while in others, the second panel is not intended to be secured to the first panel once the packaging component is opened. For example, in one embodiment, the free edge 54 of the second panel 66 is defined by a perforation line, with the second panel not being refastenable after the perforation is broken.

A plurality of absorbent articles 10, whether individually wrapped/pouched as shown in FIGS. 3-5, or otherwise wrapped, may be packaged in an outer packaging or bulk packaging component, meaning a component capable of holding two or more absorbent articles. The outer or bulk packaging component is typically the packaging used to provide the absorbent products to consumers on store shelves. The outer or bulk packaging typically provided consumers with a convenient means to transport the absorbent articles from the retailer to their home or other place of use. In one embodiment, the packaging component is formed as a bag having at least one side seal securing a pair of edges of the bag together. In other embodiments, the plurality of absorbent articles is packaged in a box or carton. The bags may be prepared from a non-woven material, polymer film, paper, laminate, and/or cloth (including woven) materials, and combinations thereof. Boxes or cartons may be prepared from materials such as cardboard, paperboard and the like.

In the present invention, the personal care product may have a packaging component graphic and an absorbent article component graphic visible through the packaging component that together form a compound coordinated graphic. To provide the compound coordinated graphic, the first graphic is different from the second graphic and the first graphic contrasts with the second graphic. As used herein, the term "contrast" means to differ in pattern complexity value, the number of colors, and/or the color intensity.

For example, in one embodiment, a single absorbent article is contained within a wrapper/pouch. The absorbent article includes a first graphic and the wrapper/pouch includes a second graphic which is different than the first graphic. The wrapper/pouch is at least partially translucent and the absorbent article is arranged in the wrapper/pouch such that at least a portion of the first graphic is visible through the wrapper/pouch. The first graphic contrasts with the second graphic in that the first graphic differs from the second graphic in complexity. The complexity of a given graphic can be determined by using the Pattern Complexity Value (PCV or complexity value) measurement method described herein.

Generally, the Pattern Complexity Value (PCV) method determines a numeric value of complexity for a graphic pattern via a combination of specific image analysis measurement parameters. The PCV method is performed using conventional optical image analysis techniques to detect graphic patterns and measure the complexity of the graphic patterns when viewed using a camera with incident lighting. An image analysis system controlled by an algorithm detects and measures several of the dimensional properties of the graphic pattern. The resulting dimensional measurement data are combined to calculate the PCV of a given pattern.

The method for determining the PCV also includes the step of preparing the sample. For feminine pads, the sample preparation includes opening the outer packaging component (if present) and removing the pouches containing feminine pads. Random individual samples are selected for analysis. The selected samples are opened by removing any feminine pads from the remaining packaging (i.e., wrapper pouches). The sample preparation also includes removing the peelstrip from the garment side of the feminine pad. The pouch, peelstrip, and any other product component are kept together for further analysis and comparison.

Figure 6:
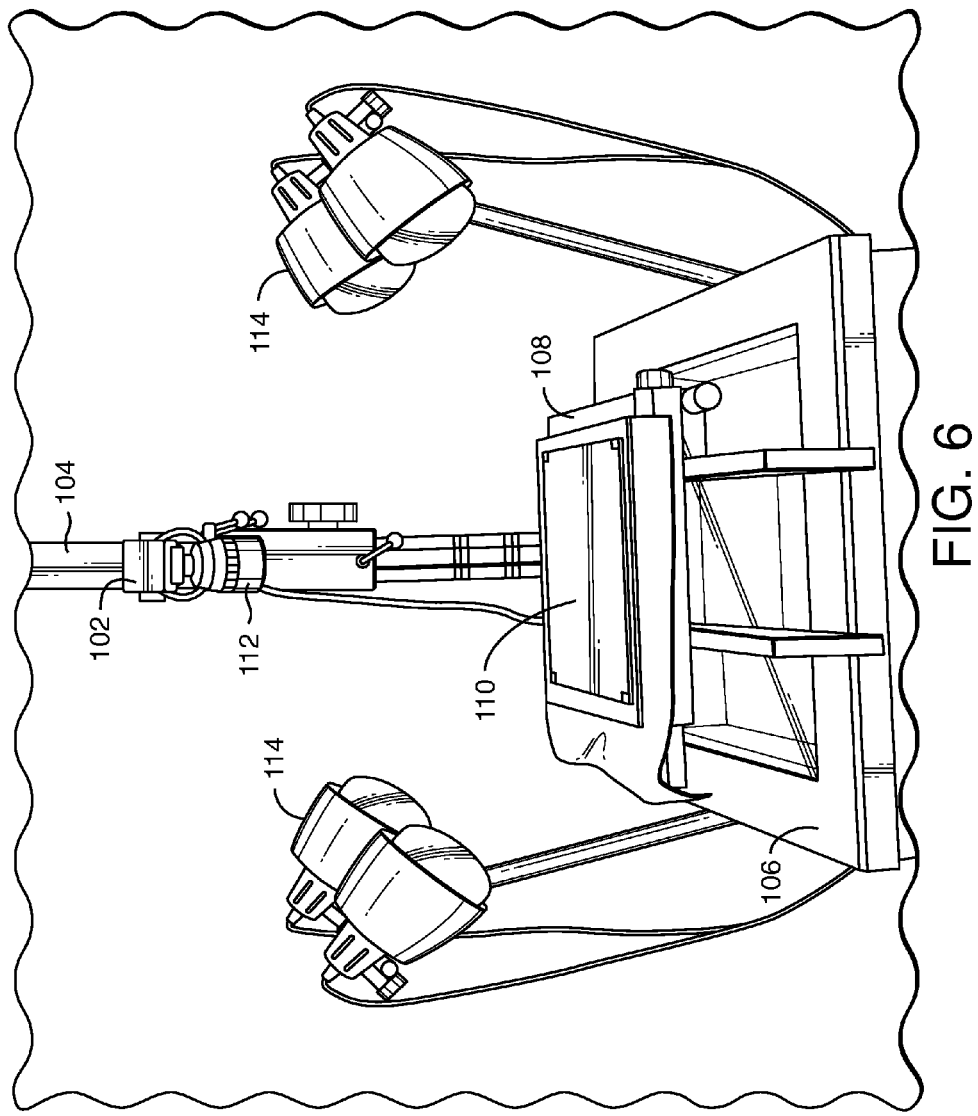
FIG. 6 is a schematic illustration of an exemplary apparatus set up to measure Pattern Complexity Values.

The method for determining the PCV of a given sample also includes the step of acquiring the image of the sample. An exemplary setup for acquiring the image is representatively illustrated in FIG. 6. Specifically, a CCD video camera 102 (e.g., a Leica DFC 310 FX video camera available from Leica Microsystems of Heerbrugg, Switzerland) is mounted on a standard support 104 such as a Polaroid MP-4 Land Camera standard support available from Polaroid Resource Center in Cambridge, Mass. The standard support 104 is attached to a macro-viewer 106 such as a KREONITE macro-viewer available from Kreonite, Inc., having an office in Wichita, Kans. An auto stage 108 is placed on the upper surface of the macro-viewer 106. The auto stage 108 is used to move and adjust the position, via a joystick, of a given sample 110 for optimal viewing by the video camera 102. A suitable auto stage is Model H112, available from Prior Scientific Inc., having an office in Rockland, Mass.

The sample 110 possessing a printed graphic pattern is placed on the auto stage 108 of a Leica Microsystems QWIN Pro Image Analysis system, under the optical axis of a 20 mm Nikon AF Nikkor lens 112 with an f-stop setting of 4. The Nikon lens 112 is attached to the Leica DFC 310 FX camera 102 using a c-mount adaptor. The distance from the front face of the Nikon lens 112 to the sample 110 is approximately 43 cm. The sample 110 is flattened and any wrinkles removed by covering it with a transparent glass plate and/or fastening it to the auto stage 108 surface using transparent adhesive tape at its outer edges. The sample 110 is illuminated with incident incandescent lighting using four, 150 watt, GE Reflector Flood lamps 114. The lamps 114 are attached to the KREONITE macro-viewer 106. The illumination level of the lamps is controlled with a POWERSTAT Variable Auto-transformer, type 3PN117C, available from Superior Electric, Co. having an office in Bristol, Conn.

The image analysis software platform used to acquire images and perform the dimensional measurements is a QWIN Pro (Version 3.5.1) available from Leica Microsystems, having an office in Heerbrugg, Switzerland. Prior to executing the algorithm below, the method for determining the PCV includes the step of shading correction. Additionally, if the sample includes colored graphics then color white balancing is undertaken and three command lines in the algorithm below (denoted with superscript$^a$) are changed to reflect color imaging in either red-green-blue (RGB) or hue-saturation-intensity (HSI) color space. Both the shading correction and the white balancing steps are performed using the QWIN software and a flat white background (e.g., a photographic positive from Polaroid 803 film) being illuminated by the flood lamps. The system and images are also accurately calibrated using the QWIN software and a standard ruler with metric markings at least as small as one millimeter. The calibration is performed in the horizontal dimension of the video camera image.

$^a$—Denotes command lines that must be changed to their color equivalent format prior to execution if color imaging and detection will be performed.

Thus, the method for determining the PCV of a given sample also includes the step of performing the dimensional measurements. Specifically, an image analysis algorithm is used to acquire and process images as well as perform measurements using the Quantimet User Interactive Programming System (QUIPS) language. The image analysis algorithm is reproduced below.

```
NAME = Pattern Complexity - 1a
PURPOSE = Measures 'complexity' of Patterns and Elements via various shape parameters
CONDITIONS = DFC 310 FX; monochrome or color; 20-mm Nikkon (f/4); 4-floods; white or black
back.; cover plate; MP4 pole=69 cm
AUTHOR = D. G. Biggs
Open File  ( C:\Data\29993\data.xls, channel #1 )
Open File  ( C:\Data\29993\feature data.xls, channel #2 )
REPLICATE = 0
SAMPLE = 0
```

-continued

```
SET-UP
  -- Calvalue = 0.149 mm/px
  CALVALUE = 0.149
  Calibration ( Local )
  Enter Results Header
  File Results Header ( channel #1 )
  File Line ( channel #1 )
  File Line ( channel #1 )
  File Results Header ( channel #2 )
  File Line ( channel #2 )
  File Line ( channel #2 )
  Measure frame ( x 31, y 61, Width 1330, Height 978 )
  Image frame ( x 0, y 0, Width 1392, Height 1040 )
  For ( SAMPLE = 1 to 1, step 1 )
    PauseText ( "Enter object classification (e.g. geo, element, pattern, etc.)." )
    Input ( TITLE$ )
    File ( TITLE$, channel #1 )
    File Line ( channel #1 )
    File ( TITLE$, channel #2 )
    File Line ( channel #2 )
    File ( "Object ID", channel #1 )
    File ( "Area", channel #1 )
    File ( "Perimeter", channel #1 )
    File ( "Area Fract.", channel #1 )
    File Line ( channel #1 )
    File ( "Object ID", channel #2 )
    File ( "Area", channel #2 )
    File ( "Conv. Area", channel #2 )
    File ( "Perim.", channel #2 )
    File ( "Conv. Perim.", channel #2 )
    File ( "Number", channel #2 )
    File Line ( channel #2 )
    For ( REPLICATE = 1 to 5, step 1 )
      Image frame ( x 0, y 0, Width 1392, Height 1040 )
      Binary Edit ( Clear Binary2 )
      IMAGE ACQUIRE
      ACQOUTPUT = 0
      Colour Transform ( Mono Mode ) "
      PauseText ( "Position sample for imaging." )
      Display ( Image0 (on), frames (on,on), planes (off,off,off,off,off,off), lut 0, x 0, y 0, z 1,
               Reduction off )
      Image Setup DC Twain [PAUSE] ( Camera 1, AutoExposure Off, Gain 0.00, ExposureTime
               78.43 msec, Brightness 0, Lamp 49.99 ) "
      Acquire ( into Image0 )
      ACQFILE$ = "C:\Images\29993 - Hopkins\"+TITLE$+"_"+STR$(REPLICATE)+".tif"
      Write image ( from ACQOUTPUT into file ACQFILE$ )
      Display ( Colour0 (on), frames (on,on), planes (off,off,off,off,off,off), lut 0, x 0, y 0, z 1,
               Reduction off )
      DETECTION AND IMAGE PROCESSING
      PauseText ("Adjust detection to include all printed areas. If necessary, this line can be
               changed to HSI or RGB detection thru editing.")
      Detect [PAUSE] ( blacker than 183, from Image0 into Binary0 delineated ) "
      PauseText ( "Is additional/unique image processing required? If yes, enter 1." )
      Input ( PROCESS )
      If ( PROCESS=1 )
        PauseText ( "Use Binary Amend to optimize detection. The final step must output to
Binary0." )
        Binary Amend [PAUSE] ( Open from Binary0 to Binary0, cycles 1, operator Disc, edge
erode on )
        PauseText ( "Use Binary Editing to optimize detection. The final step must output to
               Binary0." )
        Binary Edit [PAUSE] ( Reject from Binary0 to Binary0, nib Fill, width 2 )
      Else
        Goto CONTINUE
      Endif
      CONTINUE:
      Display ( Image0 (on), frames (on,on), planes (0,off,off,off,off,off), lut 0, x 0, y 0, z 1,
Reduction off )
      PauseText ( "Set Measure Frame to encompass features of interest and image frame to be
just inside the measure frame." )
      Measure frame [PAUSE] ( x 31, y 61, Width 1330, Height 978 )
      Image frame [PAUSE] ( x 0, y 0, Width 1392, Height 1040 )
      PauseText ( "If detected regions are within the image frame only, click on 'OK.'" )
      Binary Edit [PAUSE] ( Cut from Binary0 to Binary1, nib Fill, width 1 )
      Binary Logical ( C = A AND B : C Binary2, A Binary0, B Binary1 )
      MEASURE FIELD
      MFLDIMAGE = 2
      Measure field ( plane MFLDIMAGE, into FLDRESULTS(5), statistics into
        FLDSTATS(7,5) ) Selected parameters: Area, Perimeter, Area Fract
```

```
    AREA = FLDRESULTS(1)
    PERIM = FLDRESULTS(4)
    AREAFRACT = FLDRESULTS(5)
    File ( REPLICATE, channel #1, 0 digits after '.' )
    File ( AREA, channel #1, 1 digit after '.' )
    File ( PERIM, channel #1, 1 digit after '.' )
    File ( AREAFRACT, channel #1, 1 digit after '.' )
    File Line ( channel #1 )
    MEASURE FEATURES
    Feature Expression ( UserDef1 ( all features ), title Area/Perim =
PAREA(FTR)/PPERIMETER(FTR) )
        Measure feature ( plane Binary2, 8 ferets, minimum area: 6, grey image: Image0 )
          Selected parameters: Area, X FCP, Y FCP, Perimeter, ConvxPerim,
          ConvexArea
        File ( REPLICATE, channel #2, 0 digits after '.' )
        FSAREA = Field Sum of ( PAREA(FTR) )
        File ( FSAREA, channel #2, 1 digit after '.' )
        FSCONVAREA = Field Sum of ( PCONVAREA(FTR) )
        File ( FSCONVAREA, channel #2, 1 digit after '.' )
        FSPERIM = Field Sum of ( PPERIMETER(FTR) )
        File ( FSPERIM, channel #2, 1 digit after '.' )
        FSCONVPERIM = Field Sum of ( PCONVPERIM(FTR) )
        File ( FSCONVPERIM, channel #2, 1 digit after '.' )
        FSNUMBER = Field Sum of ( PACCEPTED(FTR) )
        File ( FSNUMBER, channel #2, 0 digits after '.' )
        File Line ( channel #2 )
        Binary Edit ( Clear Binary2 )
    Next ( REPLICATE )
    File Line ( channel #1 )
    File Line ( channel #2 )
  Next ( SAMPLE )
  Close File ( channel #1 )
  Close File ( channel #2 )
  END
```

$^a$Denotes command lines that must be changed to their color equivalent format prior to execution if color imaging and detection will be performed.

The QUIPS algorithm is then executed using the QWIN Pro software platform. The analyst is initially prompted to enter in sample identification information. This is followed by a prompting to enter in a base file name for saving the sample replicate specimen images. An opportunity is then given to set up and position the specimen of interest on the sample stage or platform beneath the camera. For most printed designs, a flat white background is suitable to detect the pattern in either gray-scale or color. In some cases, when the specimen is composed of a polymer film, a black background behind the flattened and unwrinkled specimen is suitable to obtain good detection of the pattern.

The sample is positioned so the longest dimension runs horizontally in the image, and the light illumination level of the four-flood lamps is adjusted using the POWERSTAT Variable Auto-transformer to obtain a white level reading of approximately 0.95. During this process of light adjustment, the QUIPS algorithm automatically displays the current white level value within a small window on the video screen. The algorithm then acquires and saves the image to a designated location—typically on the computer's hard drive. The analyst is then prompted to adjust the detection threshold in order to obtain the optimal detection that is possible. The delineation should be turned 'on' and the detection interactive window gray-scale histogram as well as visual observation should be used to ensure the best detection possible. For most printed designs, detection will be adjusted in 'black' mode in gray-scale or hue-saturation-intensity or red-green-blue mode in color. For polymer film patterns when using a black background, the gray-scale mode will likely need to be switched to 'white' mode.

After detection, the analyst is asked whether additional binary image processing is required to further optimize pattern detection. If the analyst believes additional processing will be beneficial, a value of '1' is entered into the prompting window and the analyst is given two opportunities to optimize the binary detection to match the design to the extent possible. In order to check for detected fit versus the actual pattern, the analyst can toggle the 'control' and 'B' keys on the keyboard simultaneously to turn the overlying binary image on and off. A fit is considered good when the binary image closely matches with the printed pattern with respect to its boundaries and regions within said boundaries. If no additional processing is required, the analyst clicks 'OK' without entering any value into the prompting window. If '1' is entered for additional processing, the first opportunity will be through a 'Binary Amend' window showing various options such as 'closing' and 'opening.' The analyst can experiment to find a good option by changing the output to binary1 or higher. When a specific processing step(s) have been identified, the analyst must do so in such a way so that the final output is into binary0. The second binary 'edit' processing step allows for a selection of manual interactions (e.g. reject, accept, draw, etc.) with the image to clean it up for the measurement step of the algorithm. Again, the final step within the manually editing processing step must go into binary0 for the output. If no editing is required, the analyst clicks 'OK' and allows the algorithm to proceed.

After the option of additional processing, the algorithm will then prompt the analyst to manually select both measurement and image frame regions of interest (ROI). First, the measurement frame is selected to enclose the detected pattern over as much of the sample (e.g., peel strip or pouch) as possible or at least enough to cover one unit cell if there is a pattern that repeats. Secondly, the image frame is selected to be just inside the boundaries of the previously selected measurement frame. The resulting image frame size should be two pixels less wide and long as the measurement frame and located within the measurement frame boundaries.

After the measurement and image frames have been selected, the algorithm will automatically perform measurements and output the data into two different spreadsheets. The first spreadsheet is labeled "data.xls" and is for the field data. The second spreadsheet is labeled "feature data.xls" and is for feature data. The following primary measurement parameter data will be located in the feature data.xls file after measurements and data transfer has occurred:

Area
Perimeter
Convex area
Convex perimeter
Number of features

The following primary measurement parameter data will be located in the data.xls file after measurements and data transfer has occurred. The field area and perimeter data located in the data.xls file are not used for calculations and should be within approximately 5% of those in the feature-data.xls file and may be used to collaborate the accuracy of the comparable area and perimeter data located in featuredata.xls file.

Area Fraction
Area
Perimeter

From these primary measurement parameter data, which are all totals for the selected image frame ROI, a number of secondary derived parameters can be calculated using the following calculations:

Fullness ratio=Sqrt.(area/convex area)

Convexity=convex perimeter/perimeter

Finally, the secondary parameters are combined with area fraction to calculate the PCV parameter:

PCV=(Area/Perimeter×Convexity/Fullness ratio)/Area Fraction

Multiple replicates from a single sample can be performed during a single execution of the QUIPS algorithm. Primary dimensional data will be transferred to the EXCEL spreadsheets for each replicate. Between each replicate, a new sample is placed onto the auto-stage and adjusted via a joystick for image acquisition and analysis. The final sample mean PCV parameter is based on an N=5 analysis from five, separate, product specimen subsamples. A comparison between different samples can be performed using a Student's T analysis at the 90% confidence level.

The Pattern Complexity Value method returns a complexity value for a given graphic wherein the more complex the graphic the lower the complexity value. Likewise, the less complex the graphic the higher the complexity value. In other words, graphics having a lower complexity value are more complex than graphics having a relatively higher complexity value (i.e., the PCV is inversely proportional to the complexity of the graphic).

Figure 7:
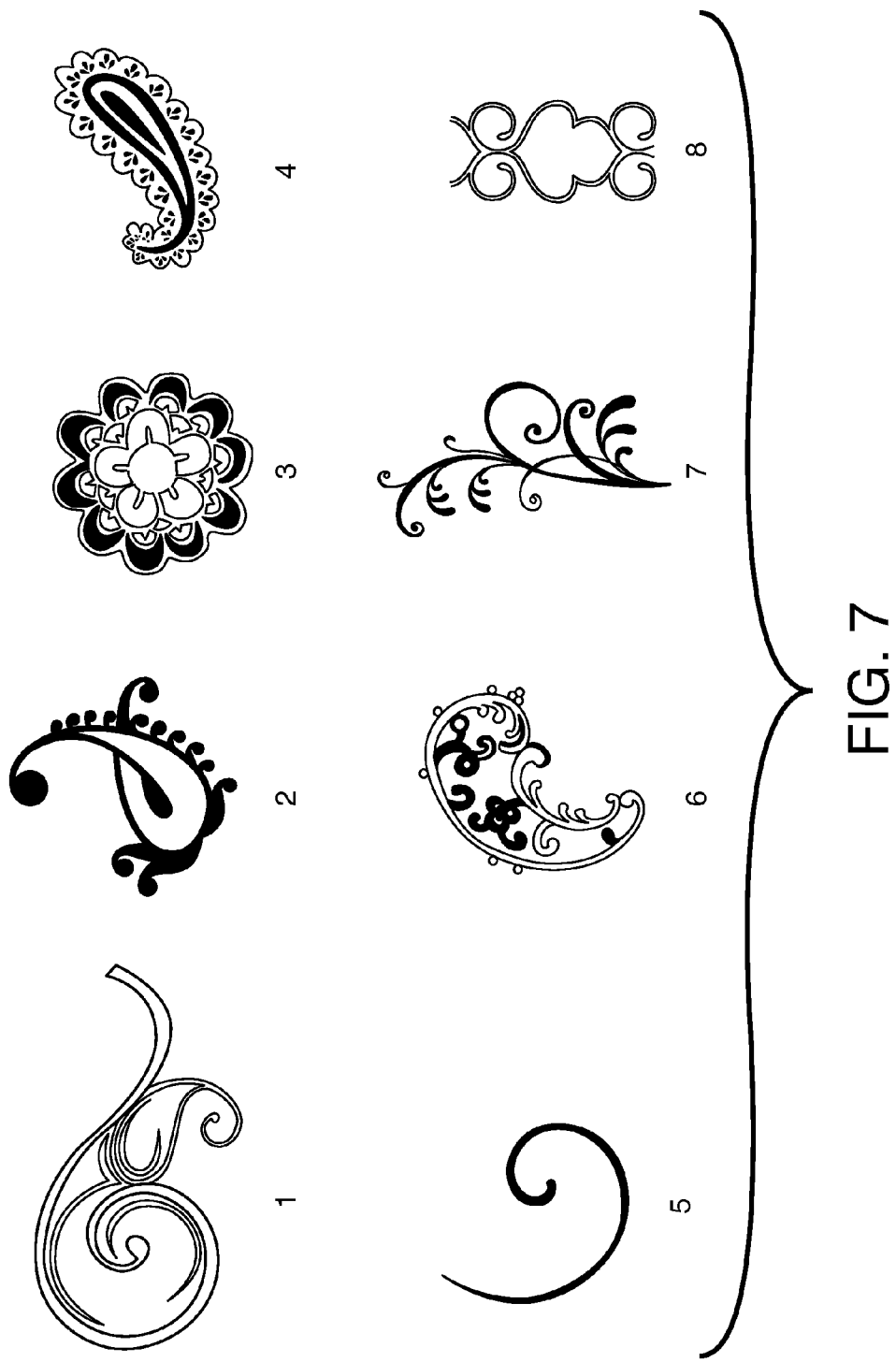
FIG. 7 representatively illustrates exemplary design elements.

To demonstrate the use of the Pattern Complexity Value method, a number of exemplary graphics were measured. Referring now to FIG. 7, the exemplary graphics are representatively illustrated and numbered 1-8. Each graphic 1-8 was measured using the Pattern Complexity Value method and the results are reproduced in Table 1 below. For these measurements, each graphic was enclosed at its outer boundaries with the smallest possible measure and image frame size that could contain the graphic.

TABLE 1

| Graphic # | Complexity Value |
|---|---|
| 1 | 13.6 |
| 2 | 24.1 |
| 3 | 9.6 |
| 4 | 13.3 |
| 5 | 32.1 |
| 6 | 5.2 |
| 7 | 15.7 |
| 8 | 7.5 |

As can be seen from Table 1, the graphics of FIG. 7 can be generally grouped into three categories: most complex (graphics 3, 6, 8), moderately complex (graphics 1, 4, 7), and least complex (graphics 2 and 5).

Figure 8:
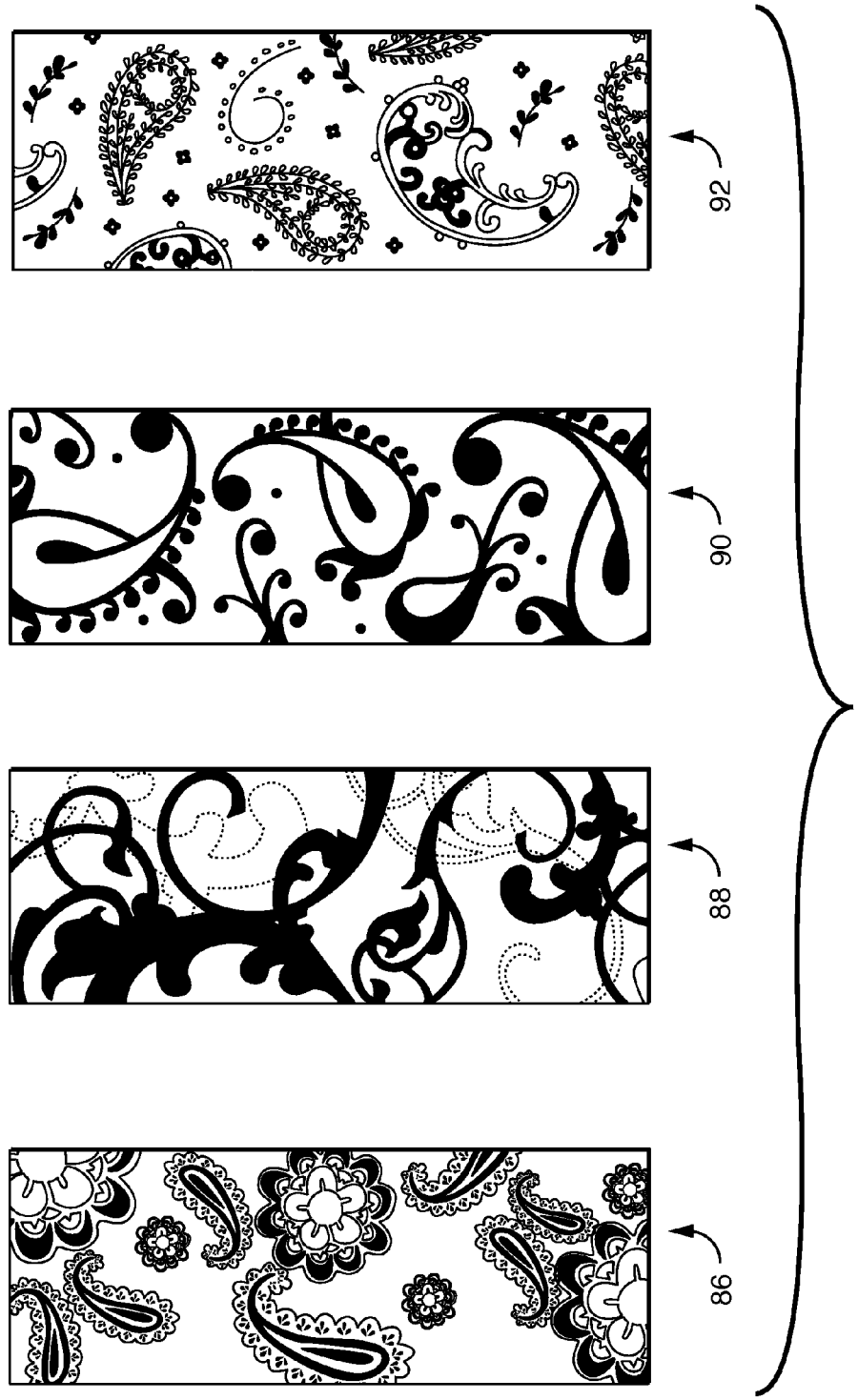
FIG. 8 representatively illustrates various printed graphics.

Referring now to FIG. 8, four exemplary graphics are illustrated as 86, 88, 90, and 92. The graphics 86-92 may be suitable for printing on a peel strip or on a pouch or on a backsheet. In particular embodiments, the graphics 86-92 of FIG. 8 may be used on a pouch 50. Again, the Pattern Complexity Value method was used to determine the relative complexity of each graphic. The results of these measurements are reproduced in Table 2 below. As can be seen from Table 2, the graphics of FIG. 8 can be generally grouped into two categories: more complex (graphics 86 and 92) and less complex (graphics 88 and 90).

TABLE 2

| Graphic # | Complexity Value |
|---|---|
| 86 | 1.51 |
| 88 | 3.86 |
| 90 | 3.17 |
| 92 | 1.22 |

Figure 9:
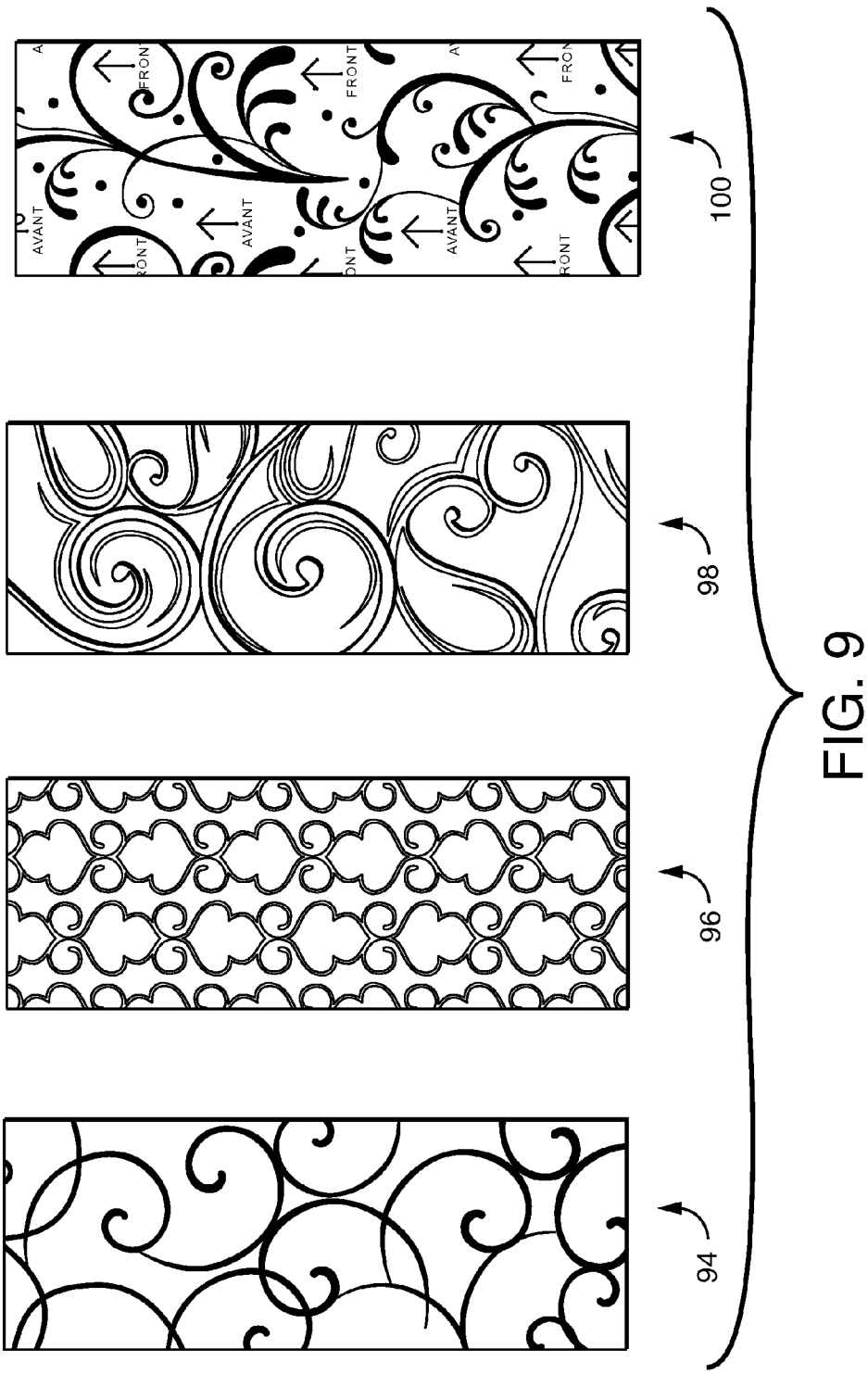
FIG. 9 representatively illustrates additional printed graphics.

Referring now to FIG. 9, four more exemplary graphics are illustrated as 94, 96, 98, and 100. The graphics 94-100 may be suitable for printing on a peel strip or a pouch or on a backsheet. In particular embodiments, the graphics 94-100 of FIG. 9 may be used on a peel strip 28. Again, the Pattern Complexity Value method was used to determine the relative complexity of each graphic. The results of these measurements are reproduced in Table 3 below.

TABLE 3

| Graphic # | Complexity Value |
|---|---|
| 94 | 5.56 |
| 96 | 4.14 |
| 98 | 3.41 |
| 100 | 3.57 |

In various embodiments, the second graphic on the pouch is at least partially aligned to overlay the first graphic on the article and to create a compound coordinated graphic. For example, in some embodiments, an article 10 may include a peel strip 28 having a graphic selected from the graphics 94-100 of FIG. 9 (first graphic). In these same embodiments, the article 10 may be packaged in a pouch 50 having a graphic selected from the graphics 86-92 of FIG. 8 (second graphic). Thus, in some embodiments, the second graphic on the pouch 50 may be aligned to at least partially overlay the first graphic on the article 10 to create a compound coordinated graphic.

Figure 10:
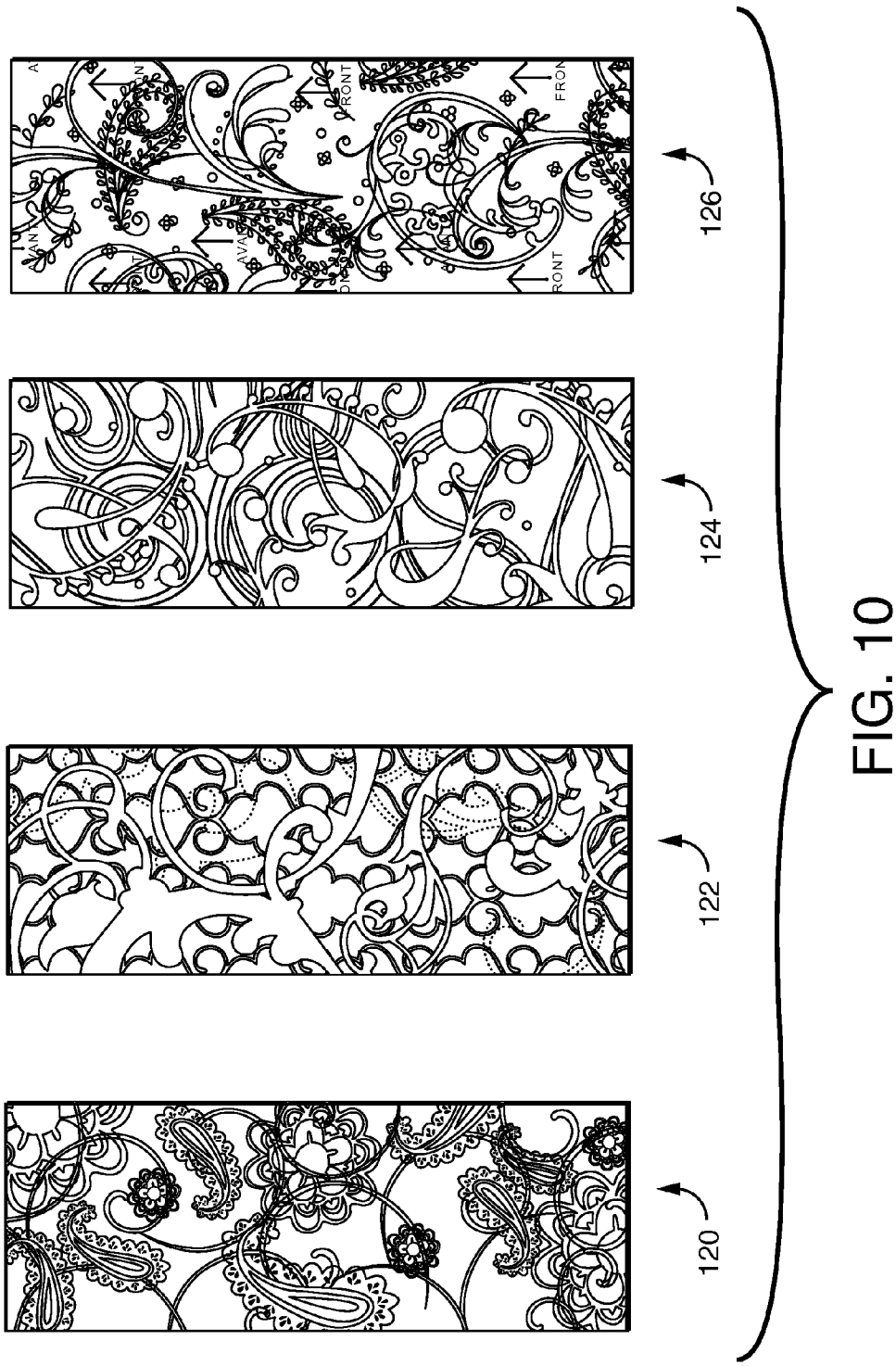
FIG. 10 representatively illustrates various compound graphics.

Referring now to FIG. 10, four compound graphics 120, 122, 124, and 126 are illustrated. Compound graphic 120 is created by a combination of graphic 86 of FIG. 8 overlaying graphic 94 of FIG. 9. Compound graphic 122 is created by a combination of graphic 88 of FIG. 8 overlaying graphic 96 of FIG. 9. Compound graphic 124 is created by a combination of graphic 90 of FIG. 8 overlaying graphic 98 of FIG. 9. Compound graphic 126 is created by a combination of graphic 92 of FIG. 8 overlaying graphic 100 of FIG. 9. In FIG. 10 some of the black fill has been omitted from the compound graphics 120-126 to better illustrate the contrasting graphics. In actual use, the pouch/wrapper material 50 is of sufficient translucency that the underlying graphics 94, 96, 98, and 100 are at least partially visible through the pouch/wrapper material and the patterns printed thereon.

TABLE 4

| Compound Graphic # | Overlay Graphic # | Overlay Complexity Value | Underlay Graphic # | Underlay Complexity | Difference in Complexity Value |
|---|---|---|---|---|---|
| 120 | 86 | 1.51 | 94 | 5.56 | 4.05 |
| 122 | 88 | 3.86 | 96 | 4.14 | 0.28 |
| 124 | 90 | 3.17 | 98 | 3.41 | 0.26 |
| 126 | 92 | 1.22 | 100 | 3.57 | 2.35 |

In general, the combination of a first graphic having very little difference in complexity as compared with a second graphic creates a less appealing and less coordinated compound graphic. For example, compound graphic 122 is constructed from graphic 96 overlaying graphic 88 or vice versa. As can be seen in Table 4, the difference in PCV between the two component graphics is very low at 0.28. As such, the component graphics do not result in a coordinated compound graphic. Likewise, compound graphic 124 is constructed from first and second graphics with a difference of only 0.26 in complexity.

In comparison, the combination of a first graphic having a relatively larger difference in complexity as compared with a second graphic is believed to create a more discreet compound graphic and a more appealing coordinated compound graphic. For example, compound graphic 120 may be constructed from component graphic 86 overlaying component graphic 94 or vice versa. As can be seen in Table 4, the difference in complexity between the two component graphics is relatively high at 4.05. As such, the component graphics 86 and 94 result in a discreet and coordinated compound graphic 120. Likewise, compound graphic 126 is constructed from component graphic 92 overlaying component graphic 100 or vice versa. The difference in complexity between the two component graphics is relatively high at 2.35. As such, the component graphics 92 and 100 result in a discreet and coordinated compound graphic 126.

Figure 11:
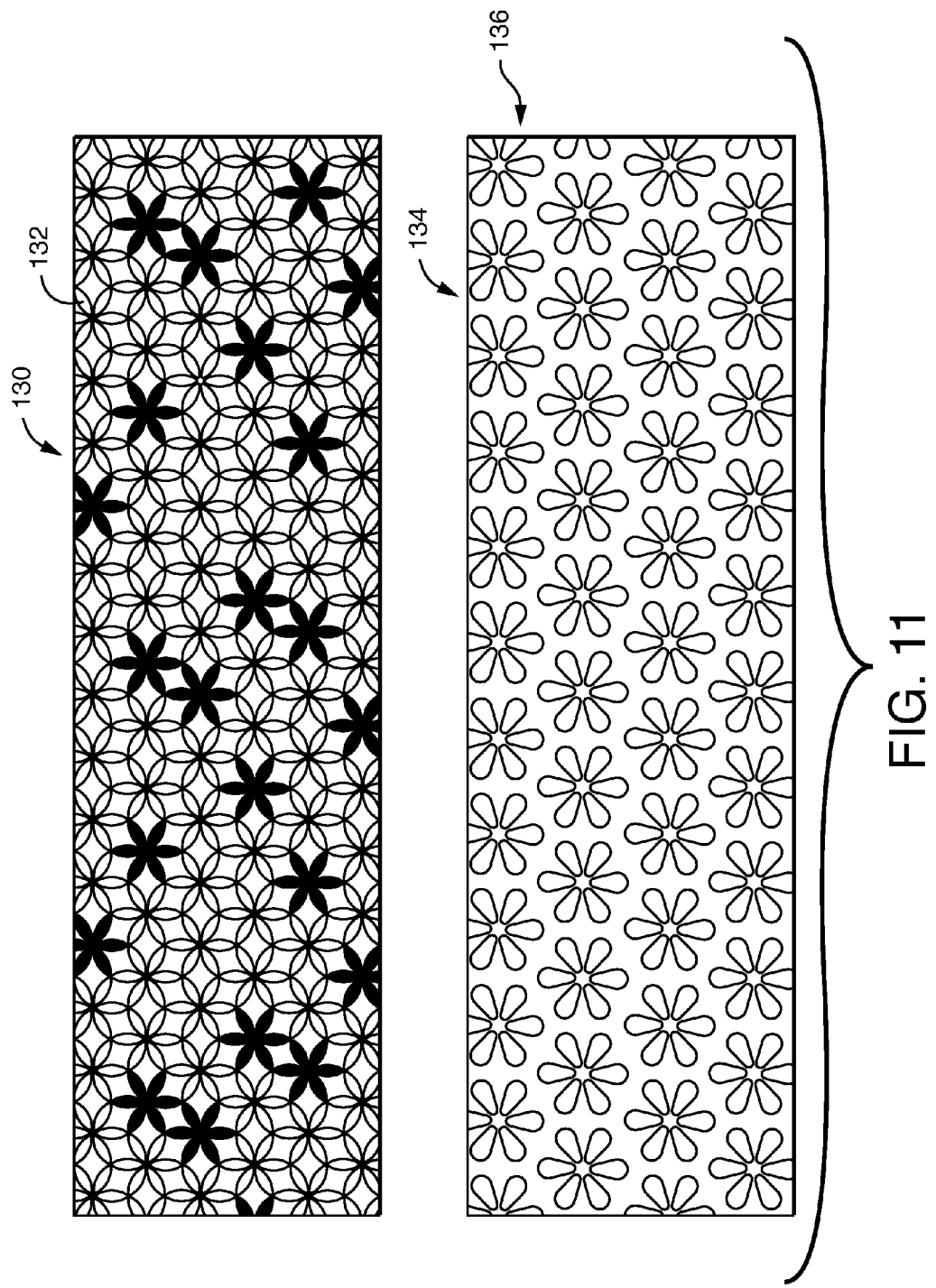
FIG. 11 representatively illustrates a peel strip and a pouch from an existing article.

Some prior art articles included printing on the peel strip and/or printing on the wrapper. However, these articles do not utilize two different component graphics having a relatively large difference in complexity values to create a discreet coordinated compound graphic like the present invention. For example, referring to FIG. 11, a commercially available peel strip removed from a Carefree 'long' pad (available from Johnson and Johnson having offices in New Jersey) is representatively illustrated at 130. The peel strip 130 includes a peel strip graphic 132. The peel strip graphic 132 includes a series of repeating flower-like elements. Additionally, FIG. 11 representatively illustrates the wrapper 134 from the same Carefree 'long' pad. The wrapper 134 includes a wrapper graphic 136. The wrapper graphic 136 includes a series of repeating flower-like elements. Together the peel strip graphic 132 and the wrapper graphic 136 combine to create a compound graphic (not shown). The PCV method was used to measure the relative complexity of the actual peel strip graphic 132 and the actual wrapper graphic 136. The results of these measurements are summarized in Table 5.

Figure 12:
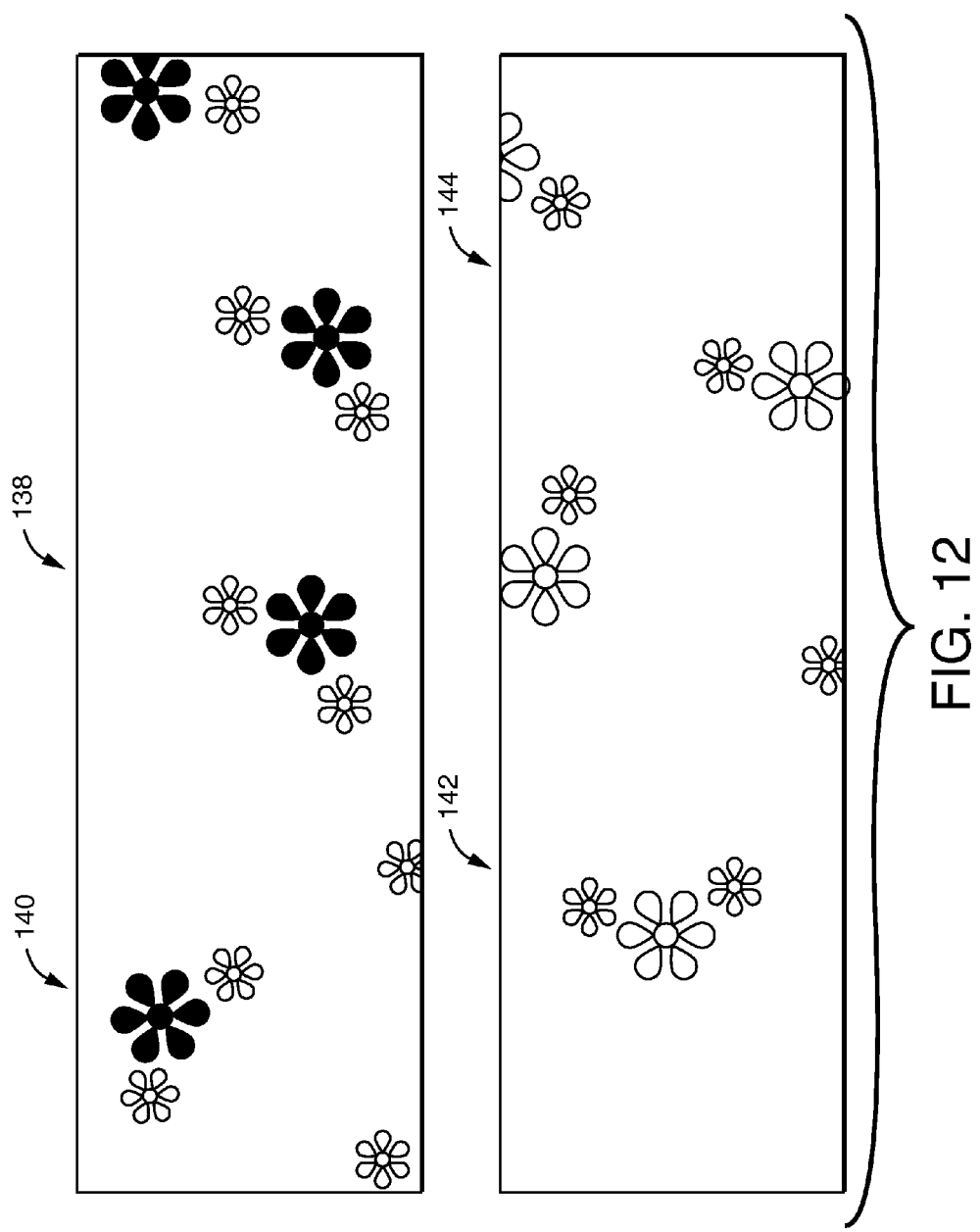
FIG. 12 representatively illustrates a peel strip and a pouch from another existing article.

Likewise, a commercially available peel strip removed from a Bella Flor feminine pad (available from Bella Flor having headquarters in Rancho Santa Fe, Calif.) is representatively illustrated at 138 in FIG. 12. The peel strip 138 includes a peel strip graphic 140. The peel strip graphic 140 includes dispersed flower-like elements of variable size. Additionally, FIG. 12 representatively illustrates the wrapper 142 from the same Bellaflora pad. The wrapper 142 includes a wrapper graphic 144. The wrapper graphic 144 includes dispersed flower-like elements of variable sizes. Together the peel strip graphic 140 and the wrapper graphic 144 combine to create a compound graphic (not shown). The PCV method was used to measure the relative complexity of the actual peel strip graphic 140 and the actual wrapper graphic 144. The results of these measurements are summarized in Table 5.

Figure 13:
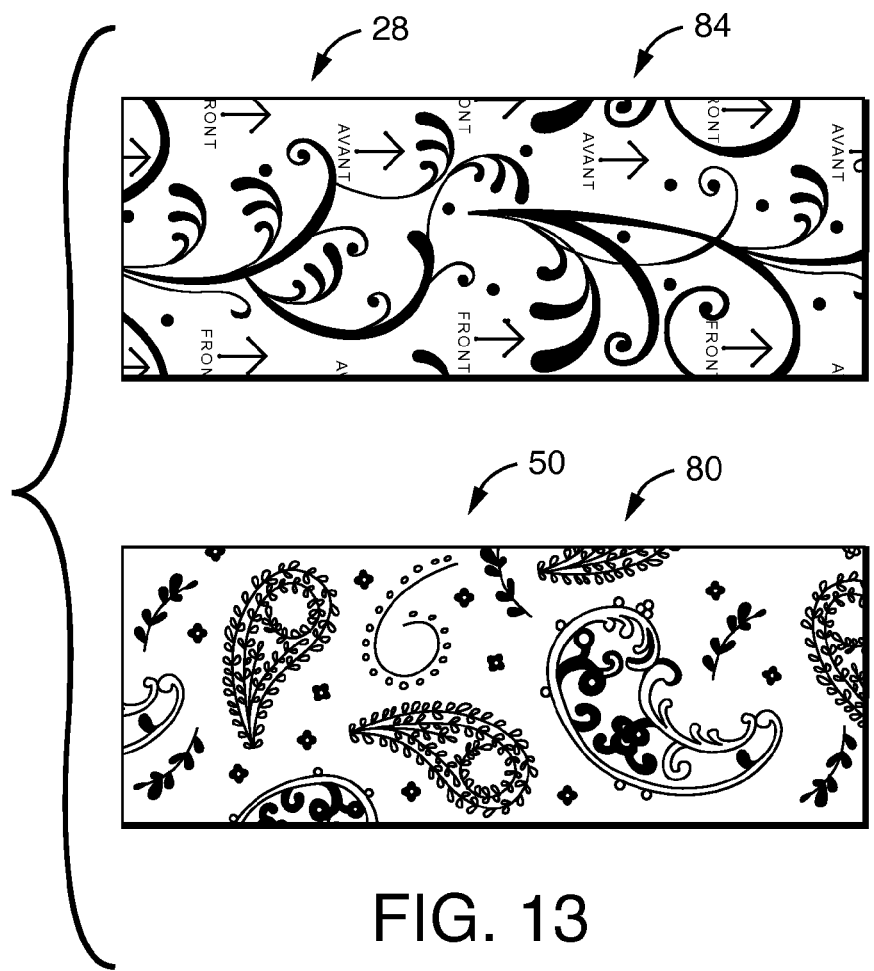
FIG. 13 representatively illustrates an exemplary peel strip and pouch of the present invention.

In comparison, an exemplary embodiment of the present invention is illustrated in FIG. 13. Specifically, FIG. 13 illustrates an exemplary peel strip 28 having a peel strip graphic 84. Additionally, FIG. 13 illustrates an exemplary pouch/wrapper 50 having a pouch graphic 80. Together the peel strip graphic 84 and the pouch graphic 80 combine to create a compound graphic 126 (FIG. 10). The PCV method was used to measure the relative complexity of the peel strip graphic 84 and the pouch graphic 80. The results of these measurements are summarized in Table 5.

TABLE 5

| Code | Overlay Graphic # | Overlay Complexity Value | Underlay Graphic # | Underlay Complexity | Difference in Complexity Value |
|---|---|---|---|---|---|
| Carefree (FIG. 11) | 136 | 1.31 | 132 | 0.78 | 0.53 |
| Bellaflora (FIG. 12) | 144 | 4.57 | 140 | 4.27 | 0.3 |
| FIG. 13 | 80 | 1.29 | 84 | 4.64 | 3.35 |

As can be seen in Table 5, the Carefree peel strip graphic 132 has PCV of 0.78 whereas the Carefree wrapper graphic 136 has a PCV of 1.31. Thus, the difference in complexity between the Carefree peel strip graphic 132 and the wrapper graphic 136 is relatively small at 0.53. In this combination both the peel strip graphic 132 and the wrapper graphic 136 were both relatively complex. Likewise, the Bella Flor peel strip graphic 140 has PCV of 4.27 whereas the Bella Flor wrapper graphic 144 has a PCV of 4.57. Thus, the difference in complexity between the Bella Flor peel strip graphic 140 and the wrapper graphic 144 is relatively small at 0.3. In this combination both the peel strip graphic 140 and the wrapper graphic 144 are both relatively simple.

In comparison, the peel strip graphic 84 of FIG. 13 has a PCV of 4.64, whereas the wrapper graphic 80 of FIG. 13 has a PCV of 1.29. Thus, the difference in complexity between the peel strip graphic 84 and the wrapper graphic 80 is relatively large at 3.35. In other words, in the combination illustrated in FIG. 13, the wrapper graphic 80 is relatively more complex than the peel strip graphic 84. This contrast is believed to better hide the absorbent article silhouette and also better hide the wrapper silhouette.

Figure 14:
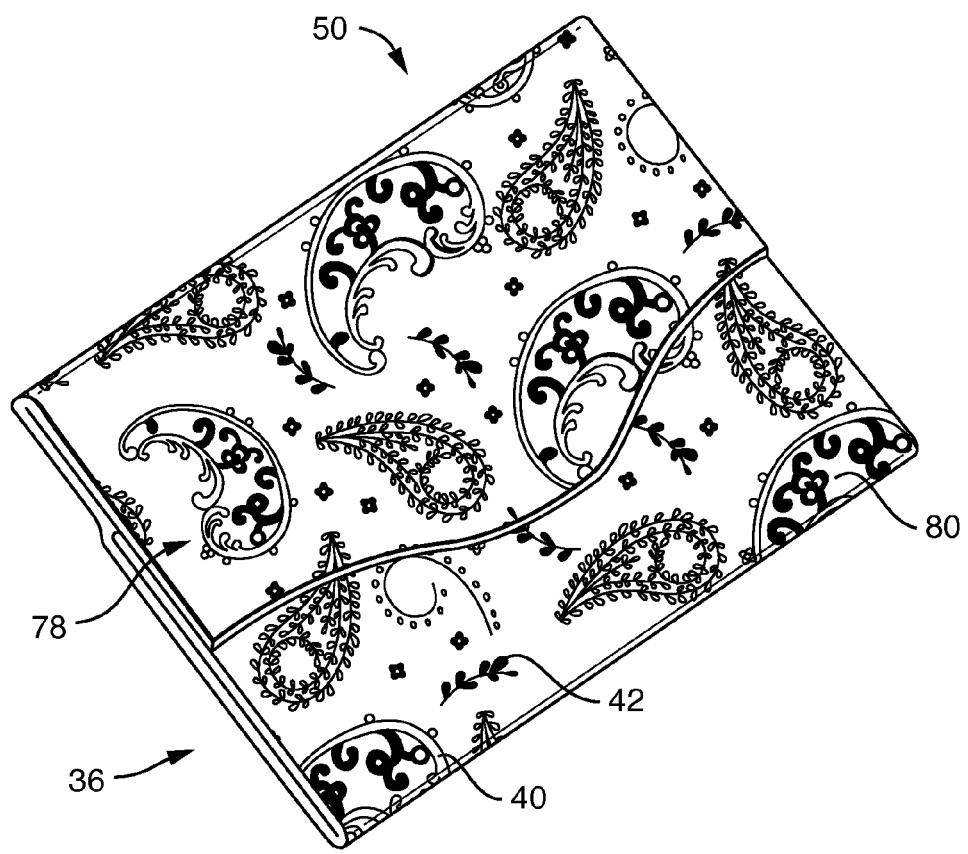
FIG. 14 representatively illustrates an exemplary pouch in the closed condition.
Figure 15:
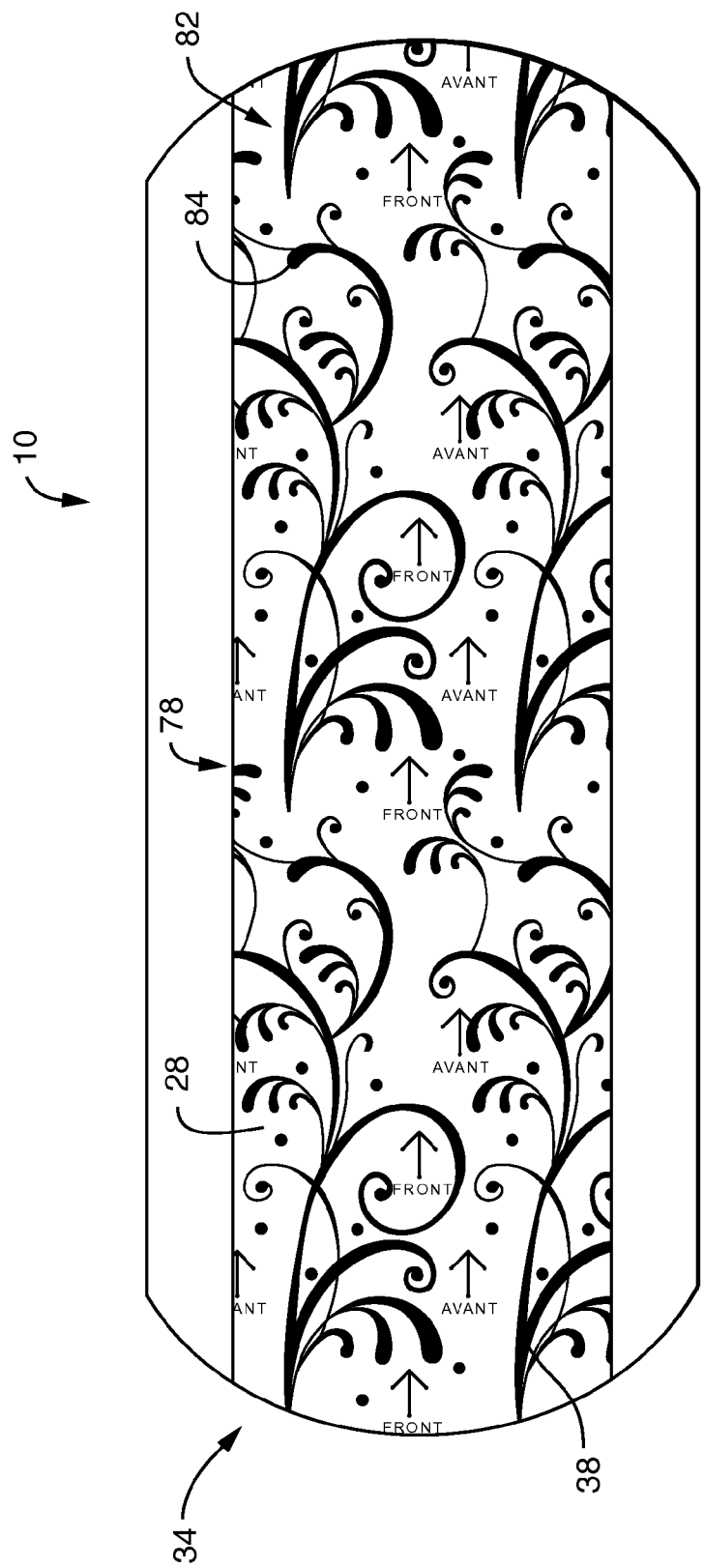
FIG. 15 representatively illustrates an exemplary article with a peel strip.

Referring now to FIG. 14, an exemplary pouch 50 is illustrated. The pouch 50 includes a pouch graphic 80 and is shown in a closed and empty configuration. Referring to FIG. 15 an exemplary absorbent article 10 is illustrated. The garment facing surface of the absorbent article 10 is illustrated and has a peel strip 28. The peel strip 28 has a peel strip graphic 82. In various embodiments, the pouch graphic 80 may be any suitable graphic ranging from the very simple to the very complex. Likewise, in various embodiments, the peel strip graphic 82 may be any suitable graphic ranging from the very simple to the very complex. In use, the peel strip graphic 82 is arranged to be visible through the pouch 50 when enclosed therein. Thus a user viewing the wrapped/pouched article will see the peel strip graphic 82 and the pouch graphic 80 combined to form a compound coordinated graphic. The compound coordinated graphic has been found to be particularly effective in providing discretion and a high quality look when the peel strip graphic 82 and the pouch graphic 80 differ in complexity. For example, the peel strip graphic 82 may be relatively less complex as compared to the pouch graphic 80 in some embodiments. Likewise, the peel strip graphic 82 may have a relatively higher complexity than the pouch graphic 80 in other embodiments. In either situation, the difference between the complexity value of the peel strip graphic 82 and the complexity value of the pouch graphic 80 is at least 1.2, at least 2, at least 3, or at least 4.

In some embodiments, the first graphic (i.e., peel strip graphic 84) may define a first complexity value of at least 3, at least 4, or at least 5. In other words, the first graphic may be relatively simple. In these embodiments, the second graphic (i.e., wrapper graphic 80) may define a second complexity value of no more than 1.2, no more than 1.5, or no more than 2. In other words, the second graphic may be relatively complex.

In other embodiments, the first graphic (i.e., peel graphic 86) may define a first complexity value of no more than 1.2, no more than 1.5, or no more than 2. In other words, the first graphic may be relatively complex. In these embodiments, the second graphic (i.e., wrapper graphic 80) may define a second complexity value of at least at least 3, at least 4, or at least 5. In other words, the second graphic may be relatively simple.

In various embodiments, the first graphic may be on the peel strip, or may be on the baffle, or may be on both the peel strip and the baffle. The peel strip may define a total peel strip area and the first graphic may be printed across 100% of the total peel strip area, or at least 80%, or at least 50% of the total peel strip area. For example, in FIG. 15, the peel strip 28 defines a total peel strip area 34 and the peel strip graphic 84 is printed across 100% of the total peel strip area 34.

In various embodiments, the baffle may define a total baffle area and the first graphic may be printed across 100% of the total baffle area, or at least 80%, or at least 50% of the total baffle area (not shown). The baffle and the peel strip may together define the entire garment facing surface area and the first graphic may be printed across 100% the total garment-facing surface area, or at least 80%, or at least 50% of the total garment facing surface area.

In various embodiments, the second graphic may be on the pouch. The pouch may define a total pouch area and the second graphic may be printed across 100% of the total pouch area, or at least 80%, or at least 50% of the total pouch area. For example, in FIG. 14, the pouch 50 defines a total pouch area 36 and the pouch graphic 80 is printed across 100% of the total pouch area 36.

In various embodiments, the present invention provides a coordinated compound graphic by utilizing a contrasting number of printed colors on the article (e.g., on the peel strip) as compared to the pouch. For example, in some embodiments, a single absorbent article is contained within a pouch wherein the absorbent article includes a first graphic and the pouch includes a second graphic. The first graphic is different than the second graphic and the pouch is at least partially translucent such that the first graphic is visible through the pouch. In these embodiments, the first graphic defines a first number of printed colors and the second graphic defines a second number of printed colors wherein the difference between the first number of printed colors and the second number of printed colors is at least one.

Figure 16:
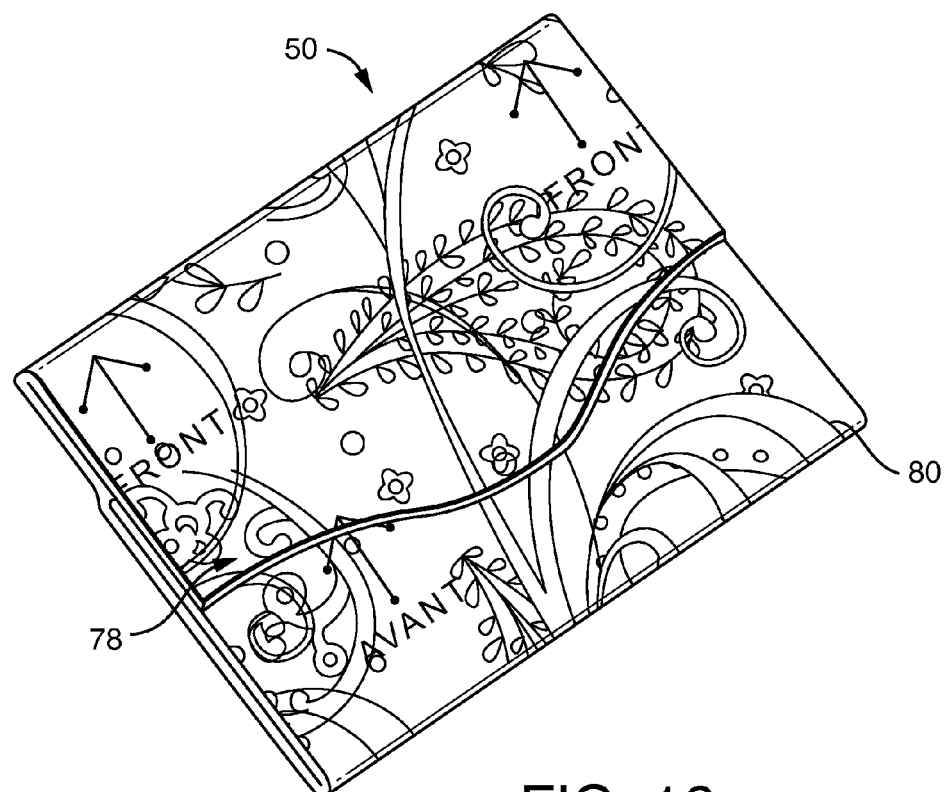
FIG. 16 representatively illustrates an exemplary article wrapped in an exemplary pouch.

Referring again to FIGS. 14 and 15, an exemplary pouch 50 and an exemplary article 10 are respectively illustrated. In some embodiments, the article 10 may be contained in the pouch 50. The article 10 includes a peel strip 28 having a peel strip graphic 84 whereas the pouch 50 includes a pouch graphic 80. The article 10 is oriented in the pouch 50 such that the peel strip graphic 84 is at least partially aligned with the pouch graphic 80. Together the peel strip graphic 84 and the pouch graphic 80 combine to create a coordinated compound graphic 85 as illustrated in FIG. 16. In FIG. 16, some of the black fill has been omitted to better illustrate the coordinated compound graphic 85. In actual use, the pouch material is sufficiently translucent such that the peel strip graphic is visible through the pouch material and/or the pouch graphic 80 to create the compound graphic.

Utilizing a different number of printed colors on the peel strip as compared to the pouch is another way of creating color complexity in the coordinated compound graphic and in turn hiding the silhouette of the article. In various embodiments, the peel strip graphic 84 may have one, two, three, four, five, or more than five different printed colors. Likewise, the pouch graphic 80 may have one, two, three, four, five, or more than five different printed colors. In various embodiments, the number of printed peel strip graphic colors is different than the number of printed pouch graphic colors. For example, in FIG. 15 the peel strip graphic 84 has only one color 38 whereas the pouch graphic 80 has a first color 40, a second color 42, and a third color 44. Thus, the difference between the first number of printed colors and the second number of printed colors is at least two. In various embodiments, the difference between the first number of printed colors and the second number of printed colors is at least one, at least two, at least three, at least four, or at least five.

To determine the number of colors in a given graphic, color images of the given graphic patterns are acquired using the QUIPS algorithm described herein. These images can then be measured for their pattern component L*a*b* color values using a number of software packages. For example, image processing and analysis packages such as Matlab (v.6.5.1, release 13; Mathworks), Adobe Photoshop, and Media Cybernetics Image Pro Plus are all suitable for measuring L*a*b* values of various colored graphics within a given pattern. The L*a*b* value for each color of the pattern can then be used to determine the number of different colors present within the pattern. Two colors are considered different if they are just-noticeably different by a consumer. This difference is sometimes estimated by just-noticeable difference or differential threshold that has been quantified by $\Delta E^*_{ab}$ greater than 2.3 as described in ASTM D2244-09b Standard Practice for Calculation of Color Tolerances and Color Differences from Instrumentally Measured Color Coordinates and the references cited therein. Although this just-noticeable difference is sufficient, a larger difference is preferable because the additional contrast between colors is believed to enhance the perceived complexity of the color graphics.

In various embodiments, the peel strip graphic 84 is comprised of a first total number of inks and the pouch graphic 80 is comprised of a second total number of inks. In some embodiments, the difference between the first total number of inks and the second total number of inks is at least one. For example, the peel strip graphic 84 may have one, two, three, four, five, or more than five different inks. Likewise, the pouch graphic 80 may have one, two, three, four, five, or more than five different inks. In various embodiments, the total number of inks in the peel strip graphic is different than the total number of inks in the pouch graphic. In some embodiments, the difference between the first total number of inks and the second total number of inks is at least one, at least two, at least three, at least four, or at least five. In some embodiments, the difference between the first total number of inks and the second total number of inks is at least four and the second total number of inks is greater than the first total number of inks Another way of creating color complexity in the coordinated compound graphic and hiding the silhouette of the article is by utilizing different print colors having different L* values on the peel strip as compared to the pouch. In various embodiments, the peel strip graphic 84 may have one or more printed colors. Likewise, the pouch graphic 80 may have one or more printed colors. Each printed color has an L* value that can be measured by any suitable imaging software program as discussed herein. The L* scale ranges from 0 (black) to 100 (white). The L* values are determined from the perspective of the user. In other words, the graphics may be printed on either side of the wrapper/pouch material but the L* value is measured from the side visible to the user. In some embodiments, the printing is on the article side of the wrapper/pouch material. Thus, the L* value in this embodiment is determined by measuring the printing "through" the wrapper/pouch material. Likewise, the graphics printed on the peel strip are measured as viewed by the user after the wrapper/pouch material has been removed. Using ADOBE Photoshop CS5 Extended software (version 12.0$_x$64, Lab Mode, CIELAB D50), the difference between the lowest L* value measured on the peel strip graphic 84 and the lowest L* value measured on the pouch graphic 80 (as initially viewed by the user) may be at least 20, at least 15, or at least 10. In various embodiments, the lowest L* value measured for the pouch graphic 80 (as initially viewed by the user) is greater than the lowest L* value for the peel strip graphic 84. In some embodiments, the peel strip graphic 84 may have a lowest L* value of no more than 30, 35, 40, 45, or 50. In some embodiments, the pouch graphic 80 may have a lowest L* value of at least 55, 60, 65, or 70. In a specific embodiment, the peel strip graphic 84 may have a lowest L* value of about 46 and the pouch graphic 80 may have a lowest L* value of about 63.

While the invention has been described in detail with respect to specific embodiments thereof, it will be appreciated that those skilled in the art, upon attaining understanding of the foregoing, will readily appreciate alterations to, variations of, and equivalents to these embodiments. Accordingly, the scope of the present invention should be assessed as that of the appended claims and any equivalents thereto. Additionally, all combinations and/or sub-combinations of the disclosed embodiments, ranges, examples, and alternatives are also contemplated.

The invention claimed is:

1. A product comprising a single absorbent article contained within a pouch, wherein
the absorbent article includes a first graphic and the pouch includes a second graphic which is different than the first graphic,
the pouch is at least partially translucent and the absorbent article is arranged in the pouch such that at least a portion of the first graphic is visible through the pouch,
the first graphic defines a first complexity value and the second graphic defines a second complexity value wherein the difference between the first complexity value and the second complexity value is at least 1.2.

2. The product of claim 1 wherein the second graphic is aligned to at least partially overlay the first graphic to create a compound coordinated graphic.

3. The product of claim 1 wherein the first graphic defines a first complexity value of at least 3.

4. The product of claim 1 wherein the first graphic defines a first complexity value of at least 5.

5. The product of claim 3 wherein the second graphic defines a second complexity value of no more than 1.3.

6. The product of claim 1 wherein the first graphic defines a first complexity value of no more than 1.3.

7. The product of claim 6 wherein the second graphic defines a second complexity value of at least 3.

8. The product of claim 1 wherein the first graphic is printed on a peel strip and the entire peel strip defines a first complexity value of at least 3 and the second graphic is printed on the pouch and the entire pouch defines a second complexity value of no more than 1.6.

9. The product of claim 1 wherein the first graphic is printed on a peel strip and the entire peel strip defines a first complexity value of no more than 1.6 and the second graphic is printed on the pouch and the entire pouch defines a second complexity value of at least 3.

10. The product of claim 1 wherein the absorbent article includes a baffle and a peel strip wherein the baffle and the peel strip combine to create an initial garment facing surface, the first graphic is printed on the peel strip and the baffle and the entire initial garment-facing surface defines a first complexity value of at least 3 and the second graphic is printed on the wrapper and the entire wrapper defines a second complexity value of no more than 1.6.

11. The product of claim 1 wherein the difference between the first complexity value and the second complexity value is at least 3.

12. The product of claim 1 wherein the first graphic defines a first number of printed colors and the second graphic defines a second number of printed colors wherein the difference between the first number of printed colors and the second number of printed colors is at least 2.

13. A product, comprising
a single absorbent article contained within a pouch, wherein
the absorbent article includes a first graphic and the pouch includes a second graphic which is different than the first graphic,
the pouch is at least partially translucent such that the first graphic is visible through the pouch, the first graphic defines a first number of printed colors and the second graphic defines a second number of printed colors wherein the difference between the first number of printed colors and the second number of printed colors is at least one and wherein the first graphic has a lowest L* value and the second graphic has a lowest L* value that is at least 10 different than the lowest L* value of the first graphic.

14. The product of claim 13 wherein the first number of printed colors is one and the second number of printed colors is at least three.

15. The product of claim 13 wherein the first graphic is comprised of a first total number of inks and the second graphic is comprised of a second total number of inks wherein the difference between the first total number of inks and the second total number of inks is at least two.

16. A product, comprising
a single absorbent article contained within a pouch, wherein
the absorbent article includes a first graphic and the pouch includes a second graphic which is different than the first graphic,
the pouch is at least partially translucent such that the first graphic is visible through the pouch, the first graphic is comprised of a first total number of printed colors having a lowest $L^*$ value and the second graphic is comprised of a second total number of printed colors having a lowest $L^*$ value wherein the difference between the lowest $L^*$ value of the first graphic and the lowest $L^*$ value of the second graphic is at least 10.

17. The product of claim 16 wherein the first graphic is comprised of a first total number of inks and the second graphic is comprised of a second total number of inks wherein the difference between the first total number of inks and the second total number of inks is at least two.

18. The product of claim 16 wherein the first number of printed colors is one and the second number of printed colors is at least three.

19. The product of claim 16 wherein the first graphic defines a first complexity value and the second graphic defines a second complexity value wherein the difference between the first complexity value and the second complexity value is at least 2.

* * * * *